US010602945B2

(12) United States Patent
Volpe et al.

(10) Patent No.: US 10,602,945 B2
(45) Date of Patent: Mar. 31, 2020

(54) TELEMETRY OF WEARABLE MEDICAL DEVICE INFORMATION TO SECONDARY MEDICAL DEVICE OR SYSTEM

(71) Applicant: ZOLL Medical Corporation, Chelmsford, MA (US)

(72) Inventors: Shane Volpe, Saltsburg, PA (US); Gary A. Freeman, Chelmsford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 191 days.

(21) Appl. No.: 15/920,142

(22) Filed: Mar. 13, 2018

(65) Prior Publication Data

US 2019/0282115 A1    Sep. 19, 2019

(51) Int. Cl.
*A61B 5/04* (2006.01)
*A61B 5/00* (2006.01)
(Continued)

(52) U.S. Cl.
CPC .......... *A61B 5/04018* (2013.01); *A61B 5/002* (2013.01); *A61B 5/0024* (2013.01);
(Continued)

(58) Field of Classification Search
CPC ..... A61B 5/002; A61B 5/0024; A61B 5/0205; A61B 5/02438; A61B 5/04018; A61B 5/0402; A61B 5/0408
See application file for complete search history.

(56) References Cited

U.S. PATENT DOCUMENTS 4,407,288 A * 10/1983 Langer ................ A61N 1/3622
607/4
4,576,170 A    3/1986 Bradley et al.
(Continued)

FOREIGN PATENT DOCUMENTS

JP    2002509472    3/2002
JP    2002-514107    5/2002
(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ull/166/1/111.
(Continued)

*Primary Examiner* — Christopher A Flory
(74) *Attorney, Agent, or Firm* — Finch & Maloney PLLC

(57) ABSTRACT

A physiological signal monitoring system includes a single set of sensing electrodes to provide conditioned physiological signals to a primary monitoring device and a secondary monitoring device. The monitoring system includes pre-processing circuitry configured to receive a raw physiological signal. The pre-processing circuitry is configured to produce a primary physiological signal and a secondary physiological signal. Each of the primary and secondary physiological signals are conditioned. The primary conditioned physiological signal is directed to a primary monitoring device such as a hospital wearable defibrillator device. The secondary conditioned physiological signal is directed to telemetry modeling circuitry where it is further processed to output one or more telemetry signals. The one or more telemetry signals are output to a secondary monitoring device such as a three lead ECG monitoring device.
(Continued)

Thus, a single set of sensing electrodes can provide physiological signals to multiple monitoring devices.

34 Claims, 14 Drawing Sheets

(51) Int. Cl.
  *A61B 5/024* (2006.01)
  *A61B 5/0408* (2006.01)
  *A61B 5/0205* (2006.01)
  *A61B 5/0428* (2006.01)
  *G16H 40/67* (2018.01)

(52) U.S. Cl.
  CPC ........ *A61B 5/02438* (2013.01); *A61B 5/0408* (2013.01); *A61B 5/0205* (2013.01); *A61B 5/04284* (2013.01); *A61B 5/6805* (2013.01); *A61B 5/7475* (2013.01); *G16H 40/67* (2018.01)

(56) References Cited

U.S. PATENT DOCUMENTS

| | | | |
|---|---|---|---|
| 4,580,572 A | 4/1986 | Granek et al. | |
| 4,583,547 A | 4/1986 | Granek et al. | |
| 4,729,377 A | 3/1988 | Granek et al. | |
| 4,928,690 A | 5/1990 | Heilman et al. | |
| 4,991,217 A | 2/1991 | Garrett et al. | |
| 5,078,134 A | 1/1992 | Heilman et al. | |
| 5,300,093 A * | 4/1994 | Koestner | A61N 1/36521 607/32 |
| 5,381,798 A | 1/1995 | Burrows | |
| 5,741,306 A | 4/1998 | Glegyak et al. | |
| 5,929,601 A | 7/1999 | Kaib et al. | |
| 5,944,669 A | 8/1999 | Kaib | |
| 6,065,154 A | 5/2000 | Hulings et al. | |
| 6,097,982 A | 8/2000 | Glegyak et al. | |
| 6,253,099 B1 | 6/2001 | Oskin et al. | |
| 6,280,461 B1 | 8/2001 | Glegyak et al. | |
| 6,336,900 B1 | 1/2002 | Alleckson et al. | |
| 6,374,138 B1 | 4/2002 | Owen et al. | |
| 6,406,426 B1 | 6/2002 | Reuss et al. | |
| 6,418,346 B1 | 7/2002 | Nelson et al. | |
| 6,442,433 B1 | 8/2002 | Linberg | |
| 6,546,285 B1 | 4/2003 | Owen et al. | |
| 6,681,003 B2 | 1/2004 | Linder et al. | |
| 6,694,191 B2 | 2/2004 | Starkweather et al. | |
| 6,804,554 B2 | 10/2004 | Ujhelyi et al. | |
| 6,889,078 B2 | 5/2005 | Struble et al. | |
| 6,889,079 B2 | 5/2005 | Bocek et al. | |
| 6,908,437 B2 | 6/2005 | Bardy | |
| 7,149,579 B1 | 12/2006 | Koh et al. | |
| 7,340,296 B2 | 3/2008 | Stahmann et al. | |
| 7,453,354 B2 | 11/2008 | Reiter et al. | |
| 7,476,206 B2 | 1/2009 | Palazzolo et al. | |
| 7,488,293 B2 | 2/2009 | Marcovecchio et al. | |
| 7,712,373 B2 | 5/2010 | Nagle et al. | |
| 7,831,303 B2 | 11/2010 | Rueter et al. | |
| 7,974,689 B2 | 7/2011 | Volpe et al. | |
| 7,991,460 B2 | 8/2011 | Fischell et al. | |
| 8,121,683 B2 | 2/2012 | Bucher et al. | |
| 8,140,154 B2 | 3/2012 | Donnelly et al. | |
| 8,271,082 B2 | 9/2012 | Donnelly et al. | |
| 8,369,944 B2 | 2/2013 | Macho et al. | |
| 8,406,842 B2 | 3/2013 | Kaib et al. | |
| 8,543,195 B1 * | 9/2013 | Brockway | A61B 5/7203 600/300 |
| 8,644,925 B2 | 2/2014 | Volpe et al. | |
| 8,649,861 B2 | 2/2014 | Donnelly et al. | |
| 8,676,313 B2 | 3/2014 | Volpe et al. | |
| 8,706,215 B2 | 4/2014 | Kaib et al. | |
| 8,774,917 B2 | 7/2014 | Macho et al. | |
| 8,868,164 B2 * | 10/2014 | Kabakov | A61B 5/6806 600/511 |
| 8,880,196 B2 | 11/2014 | Kaib | |
| 8,897,860 B2 | 11/2014 | Volpe et al. | |
| 8,904,214 B2 | 12/2014 | Volpe et al. | |
| 9,283,399 B2 | 3/2016 | Donnelly et al. | |
| 2001/0031991 A1 | 10/2001 | Russial | |
| 2003/0004547 A1 | 1/2003 | Owen et al. | |
| 2003/0032988 A1 | 2/2003 | Fincke | |
| 2003/0095648 A1 | 5/2003 | Kaib et al. | |
| 2005/0131465 A1 | 6/2005 | Freeman et al. | |
| 2006/0211934 A1 | 9/2006 | Hassonjee et al. | |
| 2008/0033495 A1 | 2/2008 | Kumar | |
| 2008/0249591 A1 | 10/2008 | Gaw et al. | |
| 2008/0306560 A1 | 12/2008 | Macho et al. | |
| 2008/0306562 A1 | 12/2008 | Donnelly et al. | |
| 2008/0312709 A1 | 12/2008 | Volpe et al. | |
| 2009/0076349 A1 | 3/2009 | Libbus et al. | |
| 2009/0076363 A1 | 3/2009 | Bly et al. | |
| 2009/0076559 A1 | 3/2009 | Libbus et al. | |
| 2009/0177046 A1 * | 7/2009 | Zhang | A61B 5/0002 600/300 |
| 2009/0234410 A1 | 9/2009 | Libbus et al. | |
| 2009/0264792 A1 | 10/2009 | Mazar | |
| 2009/0292194 A1 | 11/2009 | Libbus et al. | |
| 2009/0312650 A1 | 12/2009 | Maile et al. | |
| 2010/0052892 A1 | 3/2010 | Allen et al. | |
| 2010/0069735 A1 | 3/2010 | Berkner | |
| 2010/0076533 A1 | 3/2010 | Dar et al. | |
| 2010/0298899 A1 | 11/2010 | Donnelly et al. | |
| 2010/0312297 A1 | 12/2010 | Volpe et al. | |
| 2011/0022105 A9 | 1/2011 | Owen et al. | |
| 2011/0115624 A1 * | 5/2011 | Tran | A61B 5/0013 340/540 |
| 2011/0170692 A1 | 7/2011 | Konrad et al. | |
| 2011/0288604 A1 | 11/2011 | Kaib et al. | |
| 2011/0288605 A1 | 11/2011 | Kaib et al. | |
| 2012/0011382 A1 | 1/2012 | Volpe et al. | |
| 2012/0112903 A1 | 5/2012 | Kaib et al. | |
| 2012/0146797 A1 | 6/2012 | Oskin et al. | |
| 2012/0150008 A1 | 6/2012 | Kaib et al. | |
| 2012/0158075 A1 | 6/2012 | Kaib et al. | |
| 2012/0283794 A1 | 11/2012 | Kaib et al. | |
| 2012/0289809 A1 | 11/2012 | Kaib et al. | |
| 2012/0293323 A1 | 11/2012 | Kaib et al. | |
| 2012/0302860 A1 | 11/2012 | Volpe et al. | |
| 2013/0013014 A1 | 1/2013 | Donnelly et al. | |
| 2013/0060149 A1 | 3/2013 | Song et al. | |
| 2013/0085538 A1 | 4/2013 | Volpe et al. | |
| 2013/0144355 A1 | 6/2013 | Macho et al. | |
| 2013/0218252 A1 | 8/2013 | Kaib et al. | |
| 2013/0231711 A1 | 9/2013 | Kaib | |
| 2013/0324868 A1 | 12/2013 | Kaib et al. | |
| 2013/0325078 A1 | 12/2013 | Whiting et al. | |
| 2013/0325096 A1 | 12/2013 | Dupelle et al. | |
| 2014/0077946 A1 * | 3/2014 | Tran | A61B 5/1112 340/539.13 |
| 2014/0163334 A1 | 6/2014 | Volpe et al. | |
| 2014/0163425 A1 * | 6/2014 | Tran | G06F 19/3418 600/595 |
| 2014/0206974 A1 | 7/2014 | Volpe et al. | |
| 2014/0277243 A1 | 9/2014 | Maskara et al. | |
| 2014/0303680 A1 | 10/2014 | Donnelly et al. | |
| 2014/0324112 A1 | 10/2014 | Macho et al. | |
| 2015/0035654 A1 | 2/2015 | Kaib et al. | |
| 2015/0039042 A1 | 2/2015 | Amsler et al. | |
| 2015/0039053 A1 | 2/2015 | Kaib et al. | |
| 2015/0080699 A1 | 3/2015 | Kaib et al. | |
| 2015/0224330 A1 | 8/2015 | Kaib et al. | |
| 2015/0279187 A1 * | 10/2015 | Kranz | G08B 21/0415 340/539.12 |
| 2016/0140834 A1 * | 5/2016 | Tran | A61B 5/0077 340/539.11 |
| 2017/0049338 A1 * | 2/2017 | Pisani | A61B 5/0002 |
| 2017/0065823 A1 | 3/2017 | Kaib et al. | |
| 2017/0319080 A1 * | 11/2017 | Albert | A61B 5/0205 |
| 2017/0347886 A1 * | 12/2017 | Tran | A61B 5/01 |
| 2018/0064356 A1 * | 3/2018 | Mendenhall | G16H 40/67 |

(56) References Cited

U.S. PATENT DOCUMENTS

| | | | | |
|---|---|---|---|---|
| 2018/0140208 A1* | 5/2018 | Pisani | ................ | A61B 5/14542 |
| 2019/0223749 A1* | 7/2019 | Toth | .................... | A61B 5/0024 |

FOREIGN PATENT DOCUMENTS

| | | |
|---|---|---|
| JP | 2008-302228 | 12/2008 |
| JP | 2008302225 | 12/2008 |
| JP | 2009510631 | 3/2009 |
| WO | 83/04171 | 12/1983 |
| WO | 1998039061 | 9/1998 |
| WO | 2004078259 | 9/2004 |
| WO | 2009122277 | 10/2009 |
| WO | 2012006524 | 1/2012 |
| WO | 2013130957 | 9/2013 |
| WO | 2014097035 | 6/2014 |

OTHER PUBLICATIONS http://web.archive.org/web/20030427001846/http:/www.lifecor.comiimagelib/imageproduct.asp. Published by LifeCor, Inc., 2002, on a webpage owned by LifeCor, Inc.

Association for the Advancement of Medical Instrumentation, ANSI/AAMI DF80:2003 Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

Zoll Medical Corporation, LifeVest Model WCD 3000 Operator's Manual, Pittsburgh, PA.

Feild et al. "Improved EASI coefficients: their derivation, values, and performance." Journal of electrocardiology 35.4 (2002): 23-33.

Tomašić, et al. "Electrocardiographic systems with reduced numbers of leads—Synthesis of the 12-lead ECG." IEEE reviews in biomedical engineering 7 (2014): 126-142.

Dower et al. "Deriving the 12-lead electrocardiogram from four (EASI) electrodes." Journal of electrocardiology 21 (1988): S182-S187.

ADAS1000 Product Highlight (2012).

Schreck et al. "Derivation of the 12-lead Electrocardiogram and 3-lead Vectorcardiogram" American Journal of Emergency Medicine, 31 (2013): 1183-1190.

* cited by examiner

TELEMETRY OF WEARABLE MEDICAL DEVICE INFORMATION TO SECONDARY MEDICAL DEVICE OR SYSTEM

BACKGROUND

The present disclosure is directed to telemetry of information collected or recorded by a wearable medical device to another medical device or system.

There are a wide variety of electronic and mechanical devices for monitoring and treating patients' medical conditions. In some examples, depending on the underlying medical condition being monitored or treated, medical devices such as cardiac monitors or defibrillators may be surgically implanted or externally connected to the patient. In some cases, physicians may use medical devices alone or in combination with drug therapies to treat conditions such as cardiac arrhythmias.

One of the deadliest cardiac arrhythmias is ventricular fibrillation, which occurs when normal, regular electrical impulses are replaced by irregular and rapid impulses, causing the heart muscle to stop normal contractions. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation (VF), ventricular tachycardia (VT), pulseless electrical activity (PEA), and asystole (heart stops all electrical activity) result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

A patient admitted to a hospital may be connected to an electrocardiogram (ECG) monitoring device. Some patients may also be prescribed certain specialized equipment such as a hospital wearable defibrillator. For example, such patients may be at risk from developing sudden cardiac arrest in the hospital. A hospital wearable defibrillator can monitor for and immediately respond to such an event within a matter of seconds.

Other example external cardiac monitoring and treatment devices include the ZOLL LifeVest® wearable cardioverter defibrillator available from ZOLL Medical Corporation, and the AED Plus also available from ZOLL Medical Corporation.

SUMMARY

An electrocardiogram (ECG) signal processing system is described herein. In certain implementations, the ECG signal processing system includes a plurality of ECG sensing electrodes configured to be placed proximate to a patient's skin and detect at least one raw ECG signal lead of the patient and an ECG node device. In some examples, the ECG node device includes an ECG pre-processing circuitry operably connected to the plurality of ECG sensing electrodes, a first ECG signal conditioning circuitry configured to condition the primary ECG signal lead and provide the conditioned primary ECG signal lead to a primary ECG monitoring system, a second ECG signal conditioning circuitry configured to be electrically isolated from the first ECG signal conditioning circuitry and configured to condition the secondary ECG signal lead, and a telemetry circuitry electrically coupled to the second ECG signal conditioning circuitry. In some examples, the ECG pre-processing circuitry is configured to receive the at least one raw ECG signal lead via the plurality of ECG sensing electrodes and process the at least one raw ECG signal lead to produce a primary ECG signal lead and a secondary ECG signal lead split from the primary ECG signal lead such that the secondary ECG signal lead is substantially the same as the primary ECG signal lead. In some examples, the telemetry circuitry includes a telemetry input configured to receive the conditioned secondary ECG signal lead and at least one input from the primary ECG monitoring system, a telemetry simulation circuitry configured to simulate one or more ECG signal conditions of the patient based on the conditioned secondary ECG signal lead and the at least one input from the primary ECG monitoring system, and a plurality of telemetry output connectors configured to provide one or more output telemetry signals based on the simulated one or more ECG signal conditions of the patient to a secondary ECG processing system.

In certain implementations of the above ECG signal processing system, the telemetry simulation circuitry includes one or more relays to disconnect the telemetry circuitry from the plurality of telemetry output connectors in response to the at least one input from the primary ECG monitoring system. In some examples, the at least one input from the primary ECG monitoring system includes one or more of an electrode falloff condition, an indication of a noise condition, and an indication of an arrhythmia condition.

In certain implementations of the above ECG signal processing system, the at least one raw ECG signal lead comprises a plurality of raw ECG signal leads, and the telemetry circuitry is configured to provide a plurality of output telemetry signals corresponding to each one of the plurality of raw ECG signal leads of the patient.

In certain implementations of the above ECG signal processing system, the simulated one or more ECG signal conditions of the patient includes an electrode falloff condition.

In certain implementations of the above ECG signal processing system, the second ECG signal conditioning circuitry is further configured to filter out one or more electrical signals applied to the patient by the primary ECG monitoring system.

In certain implementations of the above ECG signal processing system, the telemetry circuitry further includes a patient model comprising a resistor network configured to model one or more electrical parameters of the patient. In some examples, the telemetry simulation circuitry is further configured to simulate the one or more ECG signal conditions by directing the conditioned secondary ECG signal lead through the resistor network. In some examples, the simulated one or more ECG signal conditions comprise a noise condition and an arrhythmia condition.

In certain implementations of the above ECG signal processing system, the telemetry circuitry is further configured to wirelessly provide the one or more output telemetry signals to the secondary ECG processing system.

In certain implementations of the above ECG signal processing system, conditioning the secondary ECG signal lead includes at least one of performing noise filtering, performing signal amplification, and performing analog to digital conversion on the secondary ECG signal lead.

In certain implementations of the above ECG signal processing system, the ECG signal processing system further includes one or more sensors configured to detect at least one of a cardio-vibrational signal, a pulmonary-vibrational signal, and a pulse oxygen level of the patient.

In certain implementations of the above ECG signal processing system, the secondary ECG processing system comprises one of a three ECG lead telemetry device, a six lead ECG monitoring device, and a twelve lead ECG monitoring device.

In certain implementations of the above ECG signal processing system, the ECG signal processing system further includes at least two therapy electrodes configured to be placed proximate to the patient's skin and further configured to deliver at least one therapeutic shock to the patient.

In certain implementations of the above ECG signal processing system, the telemetry circuitry is isolated to protect the patient from environmental electrical noise.

An ambulatory medical device is also described herein. In certain implementations, the ambulatory medical device includes a plurality of electrocardiogram (ECG) sensing electrodes configured to be in substantially continuous contact with a patient's skin over an extended period of time and detect at least one raw ECG signal lead of the patient, an ECG monitoring circuitry coupled to the plurality of ECG sensing electrodes and configured to determine one or more cardiac arrhythmia conditions in the patient, an ECG pre-processing circuitry operably connected to the plurality of ECG sensing electrodes, a first ECG signal conditioning circuitry configured to condition the primary ECG signal lead and provide the conditioned primary ECG signal lead to the ECG monitoring circuitry, the ECG monitoring circuitry being configured to determine the one or more cardiac arrhythmia conditions in the patient based on the conditioned primary ECG signal lead, a second ECG signal conditioning circuitry configured to be electrically isolated from the primary ECG signal conditioning circuitry and configured to condition the secondary ECG signal lead, and a telemetry circuitry electrically coupled to the second ECG signal conditioning circuitry, the telemetry circuitry comprising telemetry output connectors configured to provide one or more output telemetry signals based on the conditioned secondary ECG signal lead to secondary ECG monitoring circuitry. In some examples, the ECG pre-processing circuitry is configured to receive the at least one raw ECG signal lead via the plurality of ECG sensing electrodes and process the at least one raw ECG signal lead to produce a primary ECG signal lead and a secondary ECG signal lead split from the primary ECG signal lead such that the secondary ECG signal lead is substantially the same as the primary ECG signal lead.

In certain implementations of the above ambulatory medical device, the telemetry circuitry further includes a telemetry input configured to receive the conditioned secondary ECG signal lead and at least one input from the ECG monitoring circuitry and telemetry simulation circuitry configured to simulate one or more ECG signal conditions of the patient based on the conditioned secondary ECG signal lead and the at least one input from the ECG monitoring circuitry. In some examples, the telemetry simulation circuitry further includes one or more relays to disconnect the telemetry circuitry from the plurality of telemetry output connectors in response to the at least one input from the ECG monitoring circuitry.

In certain implementations of the above ambulatory medical device, the at least one raw ECG signal lead includes a plurality of raw ECG signal leads, and the telemetry circuity is configured to provide a plurality of output telemetry signals corresponding to each one of the plurality of raw ECG signal leads of the patient.

In certain implementations of the above ambulatory medical device, the second ECG conditioning circuitry is further configured to filter out one or more electrical signals applied to the patient by the ECG monitoring circuitry.

In certain implementations of the above ambulatory medical device, the telemetry circuitry further includes a patient model comprising a resistor network configured to model one or more electrical parameters of the patient.

In certain implementations of the above ambulatory medical device, the telemetry circuitry is further configured to simulate the one or more ECG signal conditions by directing the conditioned secondary ECG signal lead through the resistor network. In some examples, the simulated one or more ECG signal conditions include a noise condition and an arrhythmia condition.

In certain implementations of the above ambulatory medical device, the telemetry circuitry is further configured to wirelessly provide the one or more output telemetry signals to the secondary ECG monitoring circuitry.

In certain implementations of the above ambulatory medical device, conditioning the secondary ECG signal lead comprises at least one of performing noise filtering, performing signal amplification, and performing analog to digital conversion on the secondary ECG signal lead.

In certain implementations of the above ambulatory medical device, the ambulatory medical device further includes one or more sensors configured to detect at least one of a cardio-vibrational signal, a pulmonary-vibrational signal, and a pulse oxygen level of the patient.

In certain implementations of the above ambulatory medical device, the secondary ECG monitoring circuitry includes one of a three ECG lead telemetry device, a six ECG lead telemetry device, and a twelve ECG lead telemetry device.

In certain implementations of the above ambulatory medical device, the ambulatory medical device further includes at least two therapy electrodes configured to be placed proximate to the patient's skin and further configured to deliver at least one therapeutic shock to the patient.

A signal processing system is also described herein. In certain implementations, the signal processing system includes at least one physiological sensor configured to be placed proximate to a patient's skin and detect at least one raw physiological signal of the patient and a physiological signal processing node device. In some examples, the physiological signal processing node device includes physiological signal pre-processing circuitry operably connected to the at least one physiological sensor, first physiological signal conditioning circuitry configured to condition the first physiological signal and provide the conditioned first physiological signal to a primary patient monitoring device, second physiological signal conditioning circuitry configured to be electrically isolated from the first physiological signal conditioning circuitry and configured to condition the second physiological signal, and telemetry circuitry electrically coupled to the second physiological signal conditioning circuitry. In some examples, the physiological signal pre-processing circuitry is configured to receive the at least one raw physiological signal via the at least one physiological sensor and process the at least one raw physiological signal to produce a first physiological signal and a second physiological signal that is substantially the same as the first physiological signal. In some examples, the telemetry circuitry includes a telemetry input configured to receive the conditioned second physiological signal, telemetry simulation circuitry configured to simulate one or more physiological conditions of the patient based on the conditioned second physiological signal, and a plurality of telemetry output connectors configured to provide one or more output telemetry signals based on the simulated one or more physiological signal conditions of the patient to a secondary physiological signal processing system.

In certain implementations of the above signal processing system, the telemetry simulation circuitry includes one or more relays to disconnect the telemetry circuitry from the plurality of telemetry output connectors in response to at least one input from the primary patient monitoring device.

In certain implementations of the above signal processing system, the second physiological signal conditioning circuitry is further configured to filter out one or more electrical signals applied to the patient by the primary patient monitoring device.

In certain implementations of the above signal processing system, the telemetry circuitry is configured to receive at least one input from the primary patient monitoring device. In some examples, the telemetry simulation circuitry is further configured to simulate the one or more physiological conditions of the patient based on the conditioned second physiological signal and the at least one input from the primary patient monitoring system. In some examples, the signal processing system further includes a plurality of electrocardiogram (ECG) sensing electrodes configured to be placed proximate to a patient's skin and detect at least one raw ECG signal lead of the patient, and wherein the telemetry simulation circuitry is further configured to simulate one or more ECG signal conditions of the patient, and wherein the telemetry output connectors are further configured to provide the one or more output telemetry signals based on the simulated one or more ECG signal conditions of the patient.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Overview

Patient monitoring devices, such as in-hospital patient monitoring devices, are often used in clinical settings to monitor and record various physiological or vital signals for a patient. For example, a patient admitted to a hospital may be connected to an in-hospital three-lead electrocardiogram (ECG) monitoring device. To obtain the physiological signals for the ECG monitoring device, a set of ECG sensors can be applied to the patient's body. For example, a set of three ECG sensors can be adhered to the patient's skin, one ECG sensor located near the patient's right shoulder (often referred to as the right arm (RA) sensor), one ECG sensor located near the patient's left shoulder (often referred to as the left arm (LA) sensor), and one ECG sensor located near the patient's left hip (often referred to as the left leg (LL) sensor). By monitoring electrical signals measured by these ECG sensors, the ECG monitoring device can measure at least three leads of the patient: lead I (RA-LA); lead II (RA-LL); and lead III (LA-LL). However, it should be noted that three lead ECG monitoring systems are described by way of example only, and additional or alternative ECG monitoring systems such as three lead, five lead, six lead, and twelve lead ECG monitoring systems can be used.

For some patients, specialized ECG monitoring and/or treatment devices such as a cardiac event monitoring device, a wearable cardioverter defibrillator (WCD), or a hospital wearable defibrillator may be prescribed and worn during a hospital stay. For example, a patient having an elevated risk of sudden cardiac death, unexplained syncope, prior symptoms of heart failure, an ejection fraction of less than 45%, and other similar patients in a state of degraded cardiac health may be prescribed a specialized device. The ECG sensing electrodes and one or more therapy electrodes of these specialized devices may be placed in similar body locations as the standard three lead ECG sensors. As such, the amount of space for placing sensors on the patient's body that will provide high quality monitoring signals is limited. Additionally, increasing the number of sensors and electrodes placed on a patient increases the patient's discomfort as each sensor is typically adhered directly to the patient's skin and, as a result of having a wire running from the sensor to a monitoring device, can pull, stretch, or otherwise cause discomfort to the patient's skin. By limiting the number of sensors used the number of associated wires is also reduced, thereby reducing the number of wires that are pulling on the patient's skin.

Figure 2A:
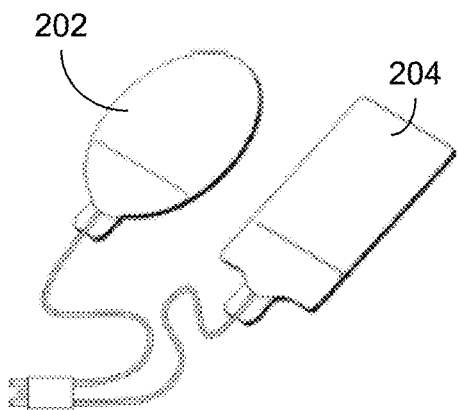
FIGS. 2A-D depict example electrodes for a wearable medical device, in accordance with an example of the present disclosure.
Figure 2B:
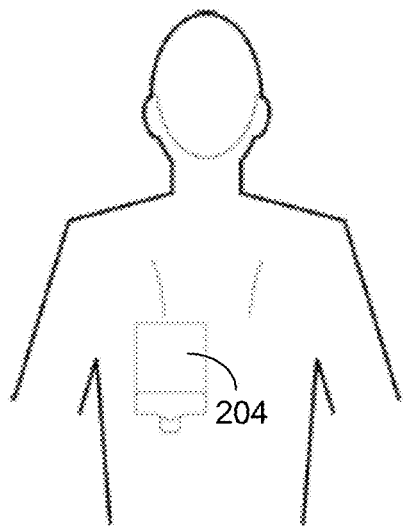
Figure 2C:
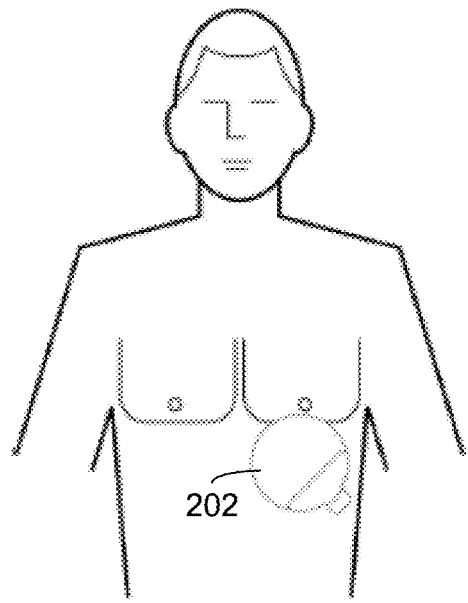
Figure 2D:
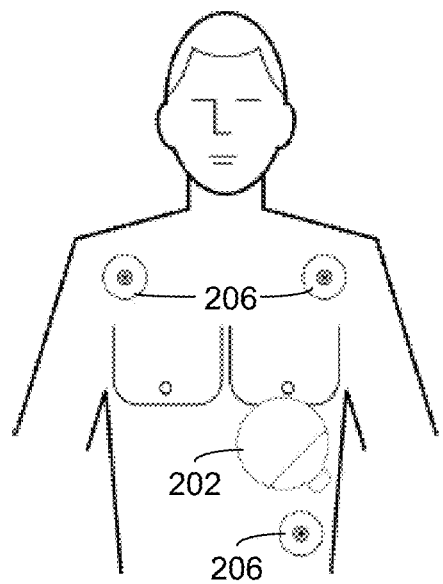

For instance, a hospital wearable defibrillator (HWD) device, such as the Hospital Wearable Defibrillator available from ZOLL Medical Corporation (Chelmsford, Mass.) in some configurations includes at least two therapy electrodes for delivering at least one therapeutic shock to the patient, three sensing electrodes for monitoring an ECG signal of the patient, and other monitoring components that are disposed on patches affixed to the patient's body. FIGS. 2A-D show example adhesive therapy electrodes and sensing electrodes of the HWD. For example, FIG. 2A illustrates an adhesive electrodes 202 and 204. FIG. 2B illustrates an example of adhesive electrode 204 adhered to a patient's back. Similarly, FIG. 2C illustrates an example of adhesive electrode 202 adhered to the patient's abdomen. FIG. 2D illustrates the patient having adhesive electrode 202 and a set of ECG sensing electrodes 206 positioned about the patient.

In yet some examples, the HWD sensor patches may be combinational patches that include both therapy and ECG sensing electrodes on a common adhesive substrate/backing. The patches for the HWD device therapy and ECG sensing electrodes may be located on similar body locations as patches for other monitoring systems.

In another instance, a wearable cardioverter defibrillator device, such as the LifeVest® Wearable Cardioverter Defibrillator from ZOLL Medical Corporation (Chelmsford, Mass.), may be prescribed to the patient. As described in further detail below, such a device includes a garment that is configured to be worn about the torso of the patient. In this case as well, there may not be room for locating patches of other monitoring systems on the patient's body. In all such instances, it thus may be beneficial to equip such specialized ECG monitoring and/or treatment devices and systems with telemetry components, modules, and/or integrated circuitry as described herein that are configured to relay the physiological signals of the patient to other medical devices or systems.

In various scenarios relevant to this disclosure, the specialized medical equipment may be regarded as a primary medical device or system for monitoring and/or recording the patient's physiological or vital signals, and from which other secondary, medical devices or systems in the in-hospital environment may receive such physiological or vital signals. Accordingly, the primary medical device can include or be externally coupled to various telemetry components, modules, and/or integrated circuitry as described herein that are configured to relay the physiological signals from the primary medical device to the secondary medical device or system.

In the context of such telemetry components, however, one or more specialized signals generated by the primary monitoring and/or treatment devices may interfere with the monitoring capabilities of the secondary medical devices. For example, a cardiac event monitoring device or a HWD device may be configured to apply an electrode falloff signal (e.g., an AC or DC signal applied as an 800 hz square or triangle wave) into the patient's body. This specialized signal may be applied from at least one ECG and/or therapy electrodes coupled to the patient's body and picked by the other ECG and/or therapy electrodes of the device. By monitoring the transmission and reception of this electrode falloff signal, a monitoring device can determine an electrode falloff condition, e.g., whether one or more of the electrodes have fallen off, lost contact with the patient's body, or is otherwise compromised such that the circuitry is no longer able to efficaciously monitor the patient's ECG signal. However, as the primary monitoring device is configured to detect this signal, the primary monitoring device can be further configured to account for this signal when monitoring patient signals. A secondary device, such as a three lead monitoring device, may not be configured to detect and account for the falloff signal and, as such, may interpret the falloff signal as noise or another anomaly that can cause signal degradation and/or a decrease in overall system quality and efficiency. Accordingly, the disclosure herein describes telemetry devices and techniques for countering such effects prior to relaying the physiological signals to secondary medical devices.

The present disclosure relates to a physiological signal monitoring system. The system utilizes a single set of sensing electrodes (or, if an HWD, a set of combination therapy and sensing electrodes) to provide conditioned physiological signals to a primary monitoring device and a secondary monitoring device. For example, the monitoring system may include pre-processing circuitry configured to receive a raw physiological signal from the sensing electrodes. The pre-processing circuitry may be further configured to produce a primary physiological signal and a secondary physiological signal that are substantially identical to the raw physiological signal. Each of the primary and secondary physiological signals may be conditioned to produce conditioned physiological signals. The primary conditioned physiological signal may be directed to a primary monitoring device associated with, for example, the HWD. The secondary conditioned physiological signal may be directed to a telemetry modeling circuitry where the secondary conditioned physiological signal is further processed to output one or more telemetry signals and simulate physiological conditions on the patient. For example, the simulated conditions can include an electrode falloff condition. When an electrode falloff event is detected, this can be reflected at the telemetry output so that the secondary device can operate based on a similar set of signals available to the primary device for a function such as electrode falloff. The one or more telemetry signals may be output to a secondary monitoring device such as a three lead ECG monitoring device, a six lead ECG monitoring device, or a twelve lead ECG monitoring device. In such an arrangement, a single set of sensing electrodes can provide physiological signals to multiple monitoring devices.

For example, a patient may be admitted to the hospital. Based upon their current cardiac condition, the patient may be required to wear a HWD in addition to a traditional three lead ECG monitoring device. An HWD, including telemetry modeling circuitry as taught herein, can be used. ECG sensing and therapy electrodes can be applied to the patient and the cardiac activity of the patient can be monitored by a primary monitoring device operably connected to the sensing and therapy electrodes. Rather than adhere additional sensors to the patient, a secondary monitoring device, such as a three lead ECG monitoring device, can be connected to, for example, an electrode node of the HWD. The secondary monitoring device can then receive modeled or conditioned telemetry signals directly from the electrode node, thereby providing for normal operation of the secondary monitoring device.

Such an approach provides several advantages over the existing techniques. For example, each monitoring device is more likely to receive a higher quality physiological signal as the single set of sensing electrodes can be positioned in locations that are most likely to produce a high quality signal. Additionally, any signals generated and transmitted into the patient by the electrodes, such as a falloff signal, can be filtered or otherwise accounted for prior to modeling the telemetry signals for monitoring by the secondary monitoring device.

Further, while this disclosure describes processing electrical signals based on underlying ECG acquired from a patient and subsequent telemetry of such signals to a secondary medical device or system, the various telemetry devices and techniques can be used to process and provide telemetry of electrical signals based on other underlying physiological sensors. For example, such physiological sensors can include vibrational sensors for producing one or more biovibrational signals (e.g., accelerometers and/or motion sensors). Such vibrational sensors can include cardio-vibrational sensors producing one or more cardio-vibrational signals, pulmonary-vibration sensors for producing one or more pulmonary-vibrational signals, breath vibration sensors, e.g., for monitoring and/or recording sleep related conditions such as snoring and sleep apnea conditions, and cardiopulmonary vibrational sensors for producing cardio-vibrational and/or pulmonary-vibrational signals based on the patient. The physiological sensors can include radio-frequency sensors for monitoring transthoracic fluid content levels, and changes relating to the same in the patient.

Further to the above noted advantages, the ability for telemetry of signals derived from a primary device to a secondary device include greater patient comfort and mobility, reduced artifact, and simpler lead placement of the primary device electrodes than placement of electrodes needed, for instance, in a twelve-lead ECG system. For example, signal artifact can be reduced due to the need for fewer electrodes on the patient and a lower chance of signal contamination or motion induced noise. The ECG electrode placement for the primary medical device and/or the electrode node can be based on a simpler ECG system than standard ECG systems. For example, the simpler ECG system can provide for relatively easy-to-locate anatomical landmarks, thus enhancing the ability to improve training of nurses, caregivers, and other in-hospital support personnel. In certain implementations, the primary device and/or external node may include a reduced-lead system comprising few electrodes from which a greater number of ECG leads can be derived for telemetry to the secondary monitoring device. Other advantages of the embodiments herein include better reproducibility in electrode placement. Further, in some implementations, fewer ECG electrodes can make it easier and faster to perform other medical procedures on the patient, such as auscultation or echocardiographic examination procedures. In addition, there can be significant cost savings due to fewer electrodes being needed for placement on the patient, simpler electronics, and a lower number of ECG channels for ECG acquisition (e.g., less expensive hardware and fewer memory requirements).

Example Specialized Medical Devices that may be Prescribed for an In-Hospital Stay The teachings of the present disclosure can be generally applied to specialized external medical monitoring and/or treatment devices (e.g., devices that are not completely implanted within the patient's body). Such specialized external medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator (HWD), a short-term wearable cardiac monitoring and/or therapeutic device, mobile cardiac event monitoring devices, and other similar wearable medical devices.

The wearable medical device can be capable of continuous use by the patient. In some implementations, the continuous use can be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. For example, the wearable medical device can be configured to be worn by a patient for as many as 24 hours a day. In some implementations, the patient may remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., electrocardiogram (ECG) information, including arrhythmia information, cardio-vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

In some implementations, the medical device may be a patient monitoring device with no treatment or therapy functions. For example, such a patient monitoring device can include a cardiac monitoring device or a cardiac monitor that is configured to monitor one or more cardiac physiological parameters of a patient, e.g., for remotely monitoring and/or diagnosing a condition of the patient. For example, such cardiac physiological parameters may include a patient's ECG information, cardio-vibrations (e.g., using accelerometers or microphones), and other related cardiac information. A cardiac monitoring device is a portable device that the patient can carry around as he or she goes about their daily routine. The cardiac monitor may be configured to detect the patient's ECG through a plurality of cardiac sensing electrodes. For example, a cardiac monitor may be attached to a patient via at least three adhesive cardiac sensing electrodes disposed about the patient's torso. Such cardiac monitors are used in mobile cardiac telemetry (MCT) and/or continuous cardiac event monitoring applications, e.g., in patient populations reporting irregular cardiac symptoms and/or conditions. Example cardiac conditions can include atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. For example, such patients may be prescribed a cardiac monitor for an extended period of time, e.g., 10 to 30 days, or more. In some mobile cardiac telemetry applications, a portable cardiac monitor can be configured to substantially continuously monitor the patient for a cardiac anomaly, and when such an anomaly is detected, the monitor may automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom). The cardiac monitor can be configured to monitor physiologic parameters of the patient other than cardiac related parameters. For example, the cardiac monitor can be configured to monitor, for example, cardio-vibrational signals (e.g., using accelerometers or microphones), pulmonary-vibrational signals, breath vibrations, sleep related parameters (e.g., snoring, sleep apnea), tissue fluids, among others.

Figure 1:
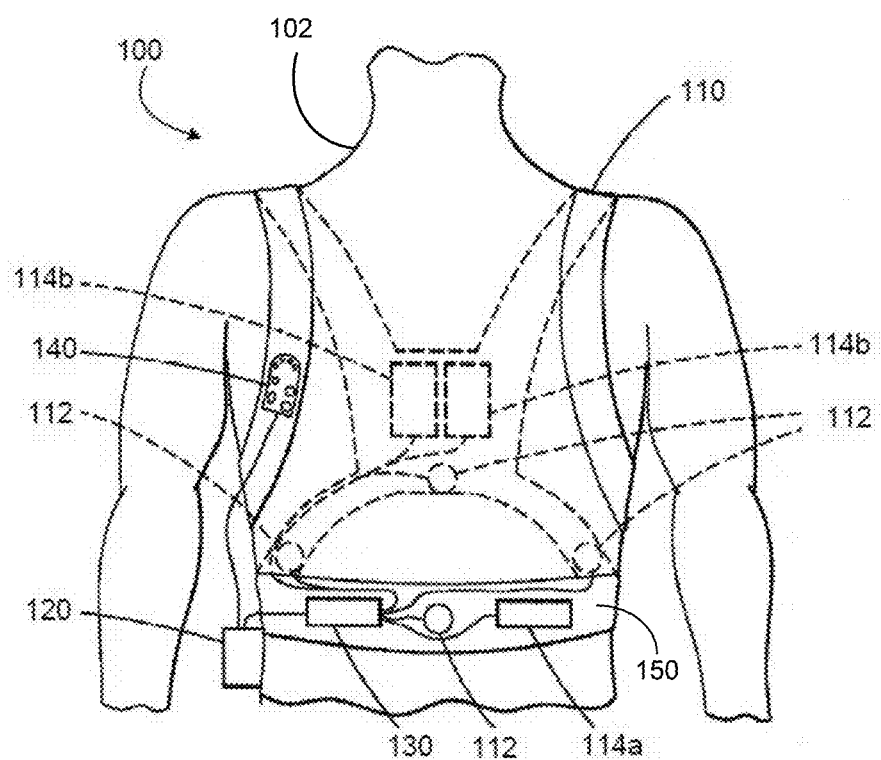
FIG. 1 depicts a wearable medical device, in accordance with an example of the present disclosure.

FIG. 1 illustrates an example medical device 100 that is external, ambulatory, and wearable by a patient 102, and configured to implement one or more configurations described herein. For example, the medical device 100 can be a non-invasive medical device configured to be located substantially external to the patient. Such a medical device 100 can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., ECG electrodes), one or more therapy electrodes 114a and 114b (collectively referred to herein as therapy electrodes 114), a medical device controller 120, a connection pod 130, a patient interface pod 140, a belt 150, or any combination of these. In some examples, at least some of the components of the medical device 100 can be configured to be affixed to the garment 110 (or in some examples, permanently integrated into the garment 110), which can be worn about the patient's torso.

The medical device controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The medical device controller 120 can be operatively coupled to the therapy electrodes 114. For example, the therapy electrodes 114 can also be assembled into the garment 110, or, in some implementations, the therapy electrodes 114 can be permanently integrated into the garment 110.

Component configurations other than those shown in FIG. 1 are possible. For example, the sensing electrodes 112 can be configured to be attached at various positions about the body of the patient 102. The sensing electrodes 112 can be operatively coupled to the medical device controller 120 through the connection pod 130. In some implementations, the sensing electrodes 112 can be adhesively attached to the patient 102. In some implementations, the sensing electrodes 112 and at least one of the therapy electrodes 114 can be included on a single integrated patch and adhesively applied to the patient's body.

The sensing electrodes 112 can be configured to detect one or more cardiac signals. Examples of such signals include ECG signals and/or other sensed cardiac physiological signals from the patient. In certain examples, the sensing electrodes 112 can include additional components such as accelerometers, acoustic signal detecting devices, and other measuring devices for recording additional parameters. For example, the sensing electrodes 112 can also be configured to detect other types of patient physiological parameters and acoustic signals, such as tissue fluid levels, cardio-vibrations, lung vibrations, respiration vibrations, patient movement, etc. Example sensing electrodes 112 include a metal electrode with an oxide coating such as tantalum pentoxide electrodes, as described in, for example, U.S. Pat. No. 6,253,099 entitled "Cardiac Monitoring Electrode Apparatus and Method," the content of which is incorporate herein by reference.

In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the medical device controller 120. One or more of the therapy electrodes 114 can be configured to deliver one or more therapeutic defibrillating shocks to the body of the patient 102 when the medical device 100 determines that such treatment is warranted based on the signals detected by the sensing electrodes 112 and processed by the medical device controller 120. Example therapy electrodes 114 can include conductive metal electrodes such as stainless steel electrodes that include one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Example Wearable Medical Device Controller

Figure 3:
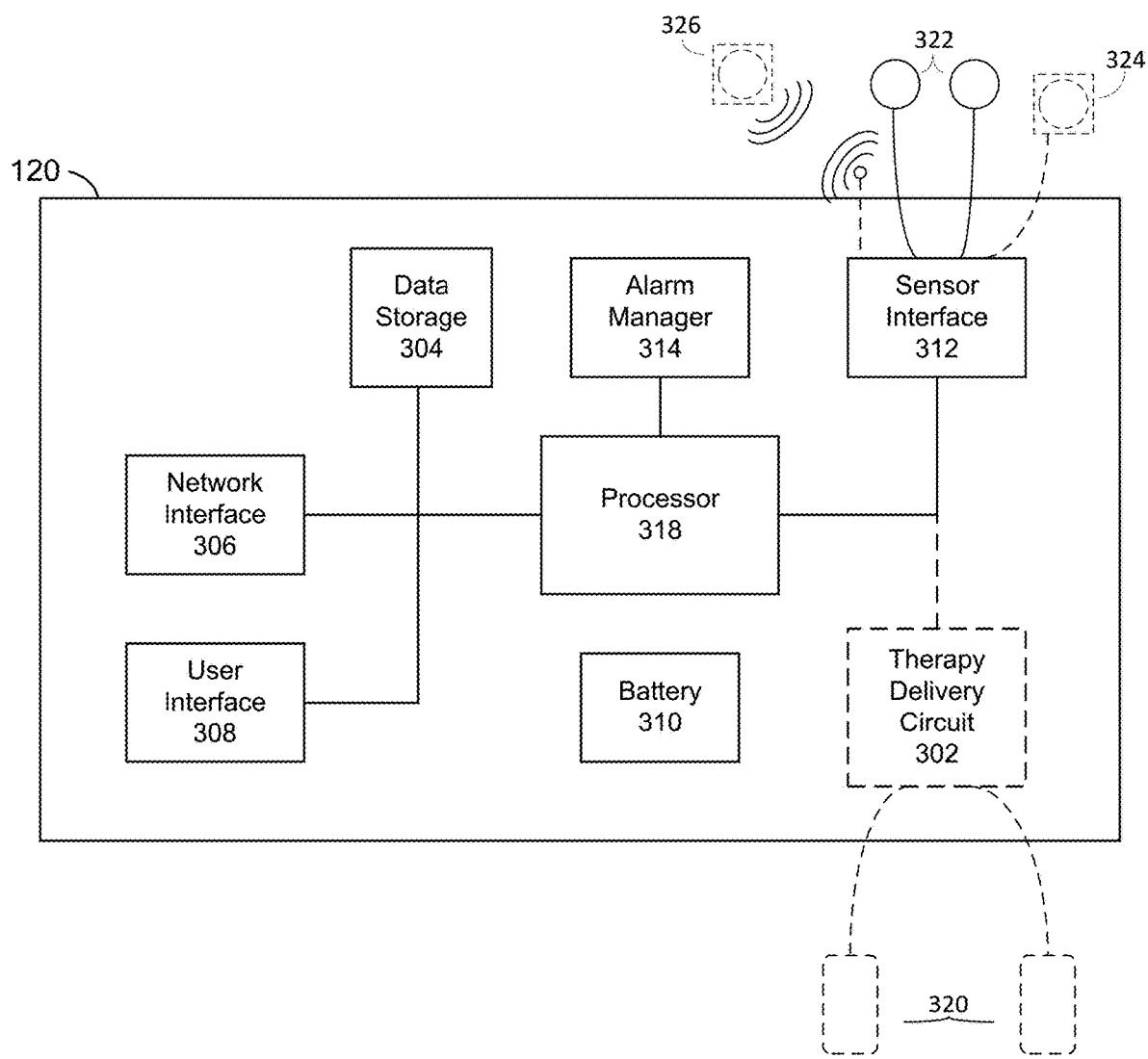
FIG. 3 depicts a schematic view of a sample controller for a wearable medical device such as that shown in FIG. 1, in accordance with an example of the present disclosure.

FIG. 3 illustrates a sample component-level view of the medical device controller 120. As shown in FIG. 3, the medical device controller 120 can include a therapy delivery circuitry 302, a data storage 304, a network interface 306, a user interface 308, at least one battery 310, a sensor interface 312, an alarm manager 314, and least one processor 318. A patient monitoring medical device can include a medical device controller 120 that includes like components as those described above, but does not include the therapy delivery circuitry 302 (shown in dotted lines).

The therapy delivery circuitry 302 can be coupled to one or more electrodes 320 configured to provide therapy to the patient (e.g., therapy electrodes 114 as described above in connection with FIG. 1). For example, the therapy delivery circuitry 302 can include, or be operably connected to, circuitry components that are configured to generate and provide the therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuitry and under control of one or more processors (e.g., processor 318) to provide, for example, at least one therapeutic shock to the patient including one or more pacing or defibrillation therapeutic pulses.

Pacing pulses can be used to treat cardiac arrhythmia conditions such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). These capacitors can be switched into a series connection during discharge for a defibrillation pulse. For example, four capacitors of approximately 650 uF can be used. The capacitors can have between 350 to 500 volt surge rating and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuitry 302 can be configured to perform the switching and pulse delivery operations, e.g., under control of the processor 218. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 304 can include one or more of non-transitory computer readable media, such as flash memory, solid state memory, magnetic memory, optical memory, cache memory, combinations thereof, and others. The data storage 304 can be configured to store executable instructions and data used for operation of the medical device controller 120. In certain examples, the data storage can include executable instructions that, when executed, are configured to cause the processor 318 to perform one or more functions.

In some examples, the network interface 306 can facilitate the communication of information between the medical device controller 120 and one or more other devices or entities over a communications network. For example, where the medical device controller 120 is included in an ambulatory medical device (such as medical device 100), the network interface 306 can be configured to communicate with a remote computing device such as a remote server or other similar computing device.

In certain examples, the user interface 308 can include one or more physical interface devices such as input devices, output devices, and combination input/output devices and a software stack configured to drive operation of the devices. These user interface elements may render visual, audio, and/or tactile content. Thus the user interface 308 may receive input or provide output, thereby enabling a user to interact with the medical device controller 120.

The medical device controller 120 can also include at least one battery 310 configured to provide power to one or more components integrated in the medical device controller 120. The battery 310 can include a rechargeable multi-cell battery pack. In one example implementation, the battery 310 can include three or more 2200 mAh lithium ion cells that provide electrical power to the other device components within the medical device controller 120. For example, the battery 310 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-b cadmium, or nickel-metal hydride) can be changed to best fit the specific application of the medical device controller 120.

The sensor interface 312 can be coupled to one or more sensors configured to monitor one or more physiological parameters of the patient. As shown, the sensors may be coupled to the medical device controller 120 via a wired or wireless connection. The sensors can include one or more electrocardiogram (ECG) electrodes 322 (e.g., similar to sensing electrodes 112 as described above in connection with FIG. 1), vibration sensor 324, and tissue fluid monitors 326 (e.g., based on ultra-wide band radiofrequency devices).

The ECG electrodes 322 can monitor a patient's ECG information. For example, the ECG electrodes 322 can be galvanic (e.g., conductive) and/or capacitive electrodes configured to measure changes in a patient's electrophysiology to measure the patient's ECG information. The ECG electrodes 322 can transmit information descriptive of the ECG signals to the sensor interface 312 for subsequent analysis.

In certain implementations, the vibration sensors 324 be configured to detect cardiac or pulmonary vibration information. For example, the vibration sensors 324 can detect a patient's heart valve vibration information. For example, the vibration sensors 324 can be configured to detect cardio-vibrational signal values including any one or all of S1, S2, S3, and S4. From these cardio-vibrational signal values or heart vibration values, certain heart vibration metrics may be calculated, including any one or more of electromechanical activation time (EMAT), percentage of EMAT (% EMAT), systolic dysfunction index (SDI), and left ventricular systolic time (LVST). The vibration sensors 324 can also be configured to detect heart wall motion, for instance, by placement of the sensor in the region of the apical beat. The vibration sensors 324 can include an vibrational sensor configured to detect vibrations from a subject's cardiac and pulmonary system and provide an output signal responsive to the detected vibrations of a targeted organ, for example, being able to detect vibrations generated in the trachea or lungs due to the flow of air during breathing. In certain implementations, additional physiological information can be determined from pulmonary-vibrational signals such as, for example, lung vibration characteristics based on sounds produced within the lungs (e.g., stridor, crackle, etc.). The vibration sensors 324 can also include a multi-channel accelerometer, for example, a three channel accelerometer configured to sense movement in each of three orthogonal axes such that patient movement/body position can be detected and correlated to detected cardio-vibrations information. The vibration sensors 324 can transmit information descriptive of the cardio-vibrations information to the sensor interface 312 for subsequent analysis.

The tissue fluid monitors 326 can use radio frequency (RF) based techniques to assess fluid levels and accumulation in a patient's body tissue. For example, the tissue fluid monitors 326 can be configured to measure fluid content in the lungs, typically for diagnosis and follow-up of pulmonary edema or lung congestion in heart failure patients. The tissue fluid monitors 326 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 326 can transmit information descriptive of the tissue fluid levels to the sensor interface 312 for subsequent analysis.

The sensor interface 312 can be coupled to any one or combination of sensing electrodes/other sensors to receive other patient data indicative of patient parameters. Once data from the sensors has been received by the sensor interface 312, the data can be directed by the processor 318 to an appropriate component within the medical device controller 120. For example, if heart data is collected by vibration sensor 324 and transmitted to the sensor interface 312, the sensor interface 312 can transmit the data to the processor 318 which, in turn, relays the data to a cardiac event detector. The cardiac event data can also be stored on the data storage 304.

In certain implementations, the alarm manager 314 can be configured to manage alarm profiles and notify one or more intended recipients of events specified within the alarm profiles as being of interest to the intended recipients. These intended recipients can include external entities such as users (patients, physicians, and monitoring personnel) as well as computer systems (monitoring systems or emergency response systems). The alarm manager 314 can be implemented using hardware or a combination of hardware and software. For instance, in some examples, the alarm manager 314 can be implemented as a software component that is stored within the data storage 304 and executed by the processor 318. In this example, the instructions included in the alarm manager 314 can cause the processor 318 to configure alarm profiles and notify intended recipients using the alarm profiles. In other examples, alarm manager 314 can be an application-specific integrated circuit (ASIC) that is coupled to the processor 318 and configured to manage alarm profiles and notify intended recipients using alarms specified within the alarm profiles. Thus, examples of alarm manager 314 are not limited to a particular hardware or software implementation.

In some implementations, the processor 318 includes one or more processors (or one or more processor cores) that each are configured to perform a series of instructions that result in manipulated data and/or control the operation of the other components of the medical device controller 120. In some implementations, when executing a specific process (e.g., cardiac monitoring), the processor 318 can be configured to make specific logic-based determinations based on input data received, and be further configured to provide one or more outputs that can be used to control or otherwise inform subsequent processing to be carried out by the processor 318 and/or other processors or circuitry with which processor 318 is communicatively coupled. Thus, the processor 318 reacts to specific input stimulus in a specific way and generates a corresponding output based on that input stimulus. In some example cases, the processor 318 can proceed through a sequence of logical transitions in which various internal register states and/or other bit cell states internal or external to the processor 318 may be set to logic high or logic low. As referred to herein, the processor 318 can be configured to execute a function where software is stored in a data store coupled to the processor 318, the software being configured to cause the processor 318 to proceed through a sequence of various logic decisions that result in the function being executed. The various components that are described herein as being executable by the processor 318 can be implemented in various forms of specialized hardware, software, or a combination thereof. For example, the processor 318 can be a digital signal processor (DSP) such as a 24-bit DSP processor. The processor 318 can be a multi-core processor, e.g., having two or more processing cores. The processor 318 can be an Advanced RISC Machine (ARM) processor such as a 32-bit ARM processor or a 64-bit ARM processor. The processor 318 can execute an embedded operating system, and include services provided by the operating system that can be used for file system manipulation, display & audio generation, basic networking, firewalling, data encryption and communications.

Telemetry Implemented with Wearable Medical Devices

As noted above, the physiological monitoring system utilizes a single set of sensing electrodes (or, if an HWD, a set of combination therapy and sensing electrodes) to provide conditioned physiological signals to a primary monitoring device and a secondary monitoring device. For example, the monitoring system may include pre-processing circuitry configured to receive a raw physiological signal from the sensing electrodes. The pre-processing circuitry may be further configured to produce a primary physiological signal and a secondary physiological signal that are substantially identical to the raw physiological signal. Each of the primary and secondary physiological signals may be conditioned to produce conditioned physiological signals. The primary conditioned physiological signal may be directed to a primary monitoring device associated with, for example, the HWD. The secondary conditioned physiological signal may be directed to a telemetry modeling circuitry where the secondary conditioned physiological signal is further processed to output one or more telemetry signals. The one or more telemetry signals may be output to a secondary monitoring device such as a three lead telemetry device. In such an arrangement, a single set of sensing electrodes can provide physiological signals to multiple monitoring devices.

For example, a patient may be admitted to the hospital. Based upon their current cardiac condition, the patient may be required to wear a HWD in addition to a traditional three lead ECG monitoring device. An HWD, including telemetry modeling circuitry as taught herein, can be used. The combinational sensing and therapy electrodes can be applied to the patient and the cardiac activity of the patient can be monitored by a primary monitoring device operably connected to the sensing and therapy electrodes. Rather than adhere additional sensors to the patient, a secondary monitoring device, such as a three lead ECG monitoring device, can be connected to, for example, an electrode node of the HWD. The secondary monitoring device can then receive modeled or conditioned telemetry signals directly from the electrode node, thereby providing for normal operation of the secondary monitoring device.

More specifically, in certain examples, an electrocardiogram (ECG) signal processing system can include a plurality of ECG sensing electrodes configured to be placed proximate to a patient's skin and detect at least one raw ECG signal lead of the patient and an ECG node device. The ECG node device can include ECG pre-processing circuitry operably connected to the plurality of ECG sensing electrodes and configured to receive the at least one raw ECG signal lead via the plurality of ECG sensing electrodes and process the at least one raw ECG signal lead to produce a primary ECG signal lead and a secondary ECG signal lead split from the primary ECG signal lead such that the secondary ECG signal lead is substantially the same as the primary ECG signal lead. The ECG node can further include first ECG signal conditioning circuitry configured to condition the primary ECG signal lead and provide the conditioned primary ECG signal lead to a primary ECG monitoring device, second ECG signal conditioning circuitry configured to be electrically isolated from the first ECG signal conditioning circuitry and configured to condition the secondary ECG signal lead, and telemetry circuitry electrically coupled to the second ECG signal conditioning circuitry. The telemetry circuitry can include a telemetry input configured to receive the conditioned secondary ECG signal lead and at least one input from the primary ECG monitoring system. The telemetry simulation circuitry can be configured to simulate one or more ECG signal conditions of the patient based on the conditioned secondary ECG signal lead and the at least one input from the primary ECG monitoring system. A plurality of telemetry output connectors can be configured to provide one or more output telemetry signals based on the simulated one or more ECG signal conditions of the patient to an secondary ECG processing system.

In another implementation, an ambulatory medical device can include a plurality of ECG sensing electrodes configured to be in substantially continuous contact with a patient's skin over an extended period of time and detect at least one raw ECG signal lead of the patient, ECG monitoring circuitry coupled to the plurality of ECG sensing electrodes and configured to determine one or more cardiac arrhythmia conditions in the patient, and ECG pre-processing circuitry operably connected to the plurality of ECG sensing electrodes and configured to receive the at least one raw ECG signal lead via the plurality of ECG sensing electrodes and process the at least one raw ECG signal lead to produce a primary ECG signal lead and a secondary ECG signal lead split from the primary ECG signal lead such that the secondary ECG signal lead is substantially the same as the primary ECG signal lead. The ambulatory medical device can further include first ECG signal conditioning circuitry configured to condition the primary ECG signal lead and provide the conditioned primary ECG signal lead to the ECG monitoring circuitry, second ECG signal conditioning circuitry configured to be electrically isolated from the primary ECG signal conditioning circuitry and configured to condition the secondary ECG signal lead, and telemetry circuitry electrically coupled to the second ECG signal conditioning circuitry, the telemetry circuitry comprising telemetry output connectors configured to provide one or more output telemetry signals based on the conditioned secondary ECG signal lead to a secondary ECG monitoring circuitry.

In another implementation, a signal processing system can include at least one physiological sensor configured to be placed proximate to a patient's skin and detect at least one raw physiological signal of the patient and a physiological signal processing node device. The physiological signal processing node can include physiological signal pre-processing circuitry operably connected to the at least one physiological sensor and configured to receive the at least one raw physiological signal via the at least one physiological sensor and process the at least one raw physiological signal to produce a first physiological signal and a second physiological signal that is substantially the same as the first physiological signal. The physiological signal processing node can further include first physiological signal conditioning circuitry configured to condition the first physiological signal and provide the conditioned first physiological signal to a primary patient monitoring device. A second physiological signal conditioning circuitry is configured to be electrically isolated from the first physiological signal conditioning circuitry. The second physiological signal conditioning circuitry is configured to condition the second physiological signal. A telemetry circuitry is electrically coupled to the second physiological signal conditioning circuitry. The telemetry circuitry can include a telemetry input configured to receive the conditioned second physiological signal. The telemetry circuitry also includes telemetry simulation circuitry configured to simulate one or more physiological conditions of the patient based on the conditioned second physiological signal. A plurality of telemetry output connectors are configured to provide one or more output telemetry signals based on the simulated one or more physiological signal conditions of the patient to a secondary physiological signal processing system.

Implementation of Telemetry Circuitry

As noted above, in certain implementations, a patient may be connected to a monitoring and/or treatment device such as a HWD in addition to a traditional ECG monitoring device, such as a three lead ECG monitoring device. In some examples, the HWD can include circuitry configured to receive physiological signals from a set of sensing electrodes on a patient and to model and/or otherwise condition expected output signals for the traditional ECG monitoring device. In such examples, the secondary monitoring device can be connected to the HWD to receive the output signals from the HWD device as opposed to having another set of sensing electrodes on the patient.

Figure 4A:
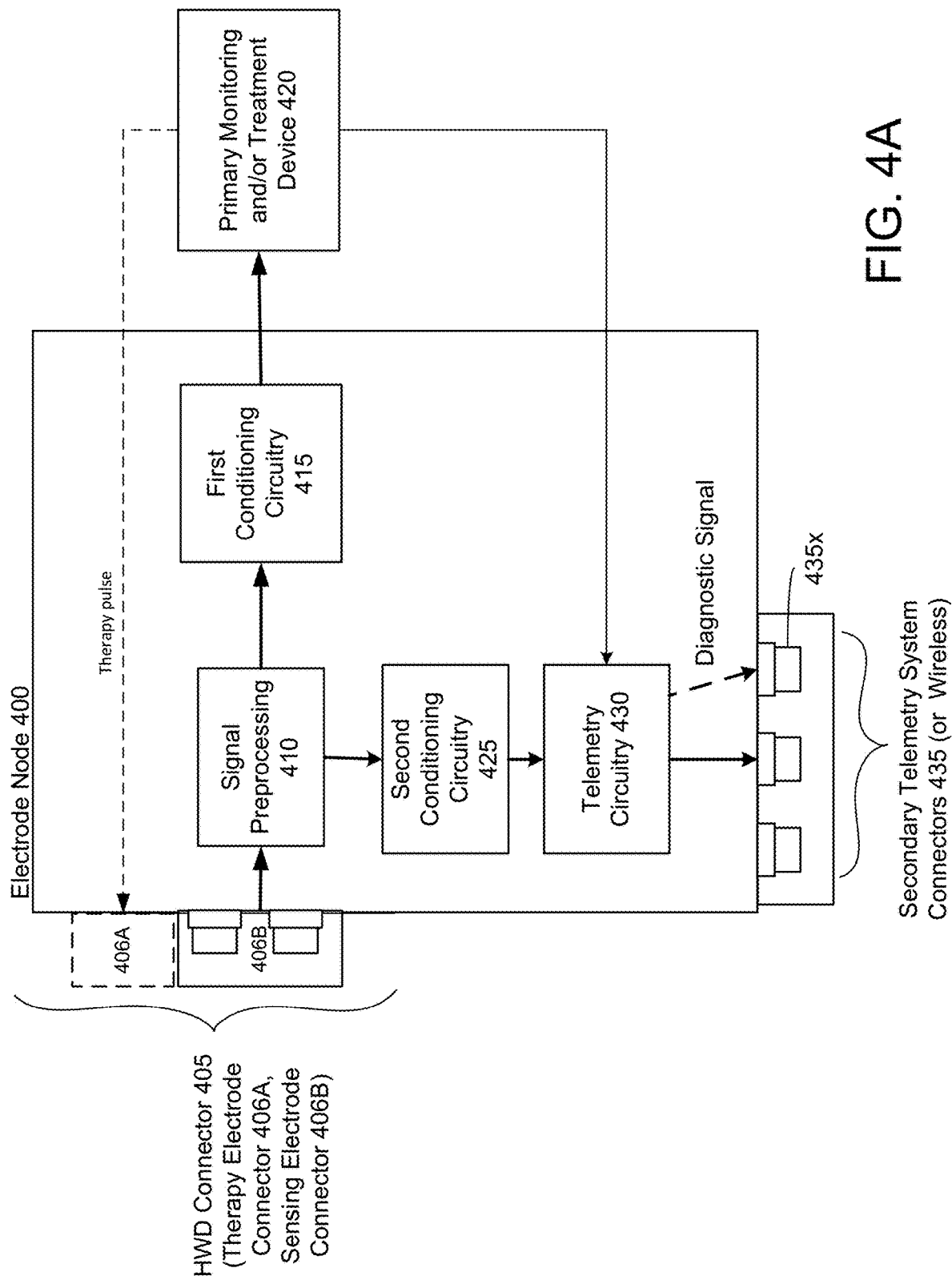
FIG. 4A depicts a schematic view of an electrode node for a wearable medical device, in accordance with an example of the present disclosure.
Figure 5A:
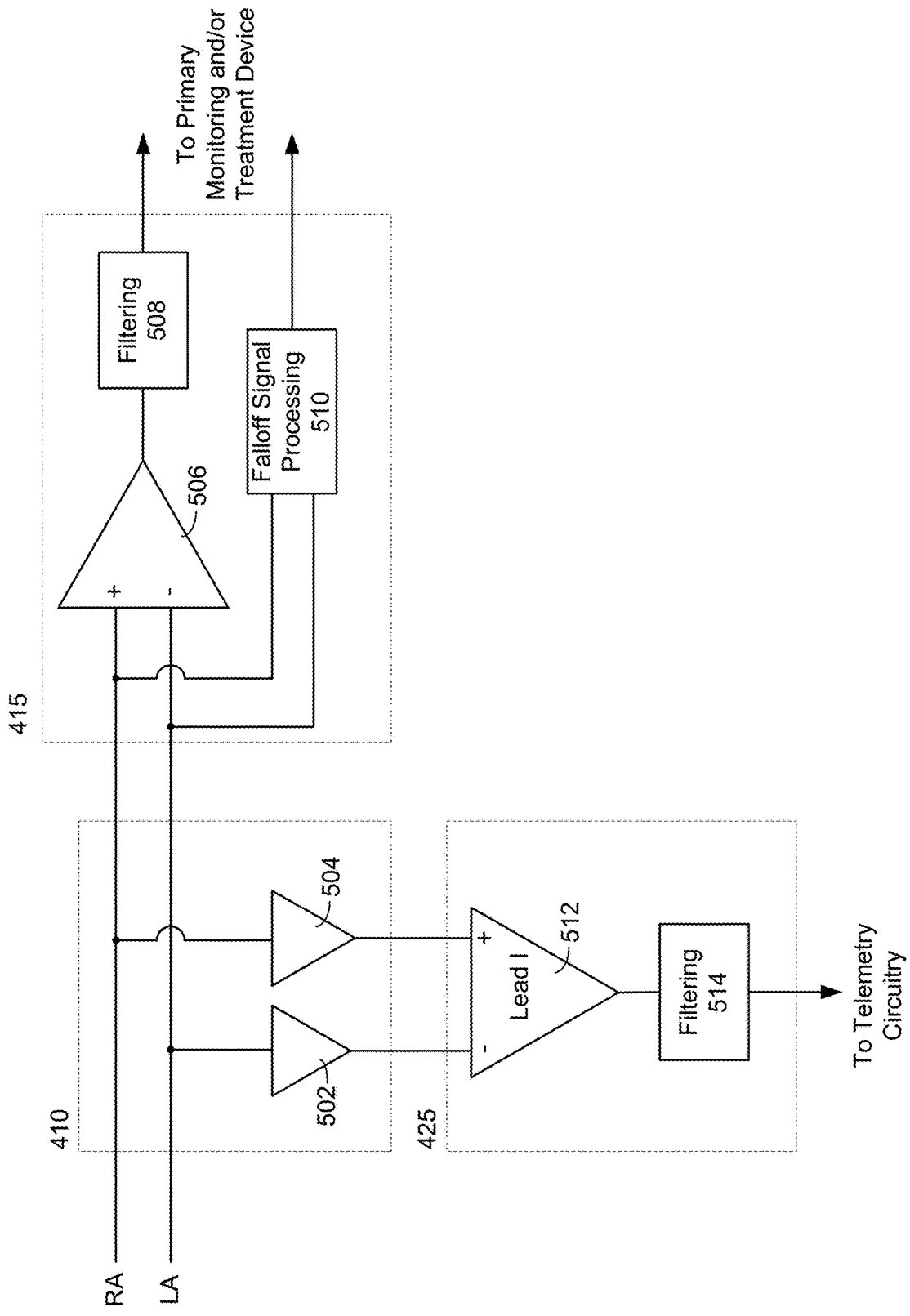
FIG. 5A depicts a sample circuitry diagram for an electrode node such as the node shown in FIG. 4, in accordance with an example of the present disclosure.
Figure 5B:
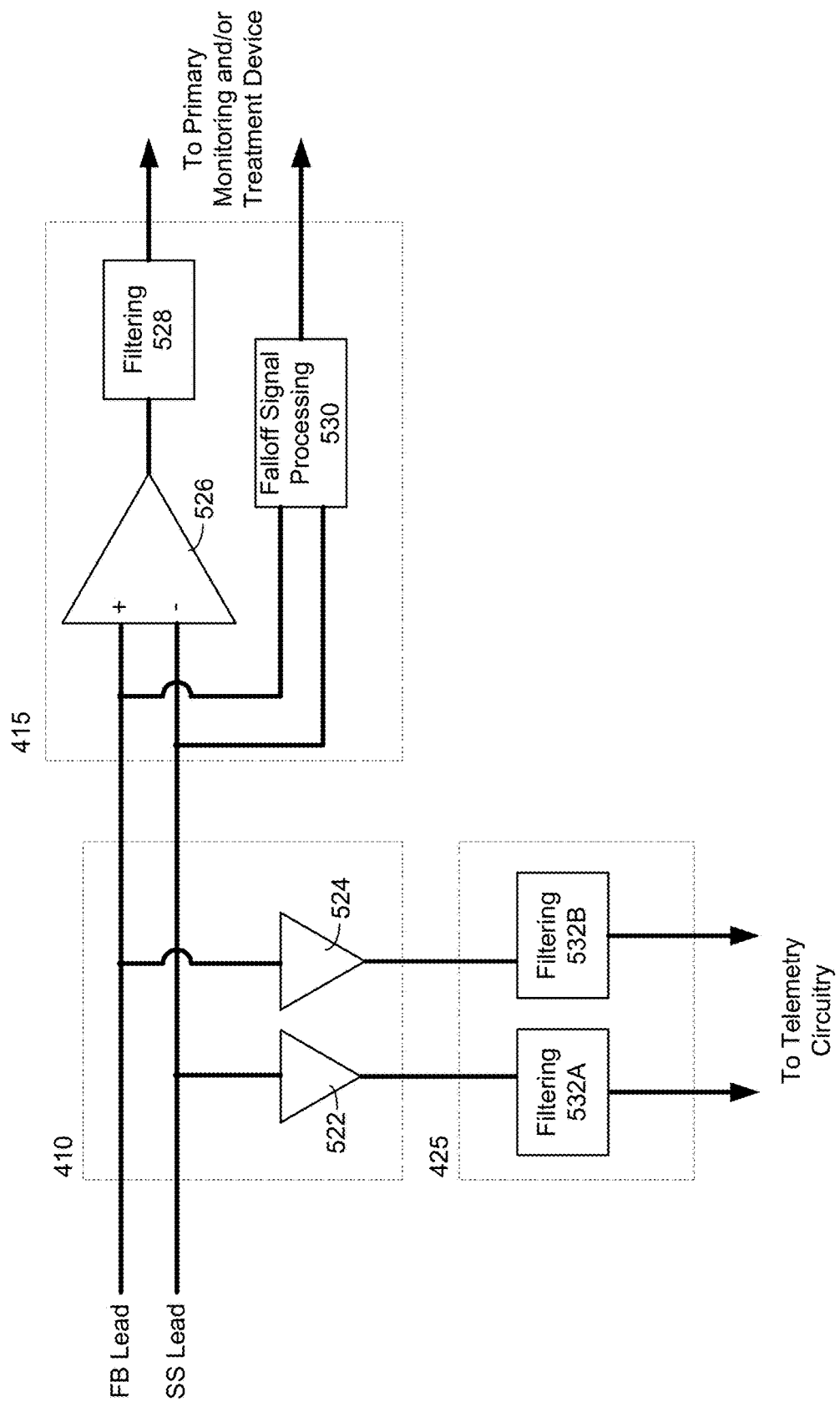
FIG. 5B depicts an alternate sample circuitry diagram for an electrode node such as the node shown in FIG. 4A, in accordance with an example of the present disclosure.

FIG. 4A illustrates a sample schematic diagram including an electrode node 400 that may be configured to receive a raw physiological signal from a set of sensing electrodes on a patient. The electrode node 400 may be further configured to process the raw physiological signal to produce two or more substantially identical copies of the raw physiological signal. FIGS. 5A and 5B, described below in concert with FIG. 4A, illustrate sample circuit-level diagrams for various components contained within the electrode node 400 as shown in FIG. 4A.

A first copy of the physiological signal can be conditioned and passed to a primary physiological monitoring device. A second copy of the physiological signal can be conditioned, processed, and passed to a secondary physiological monitoring device. In certain implementations, the primary physiological monitoring device can be a monitor associated with the monitoring and/or treatment device such as the HWD and the secondary physiological monitoring device can be an ECG monitoring device.

Referring again to FIG. 4A, the electrode node 400 can include a set of connectors 405. As noted above, in certain implementations the electrode node 400 may be integrated into a monitoring and treatment device. In such an example, the connectors 405 can include a treatment or therapy electrode connector 406A and sensor or sensing electrode connectors 406B. However, it should be noted that the techniques, processes, and teachings described herein are not limited to a treatment device and, as such, the therapy electrode connector 406A can be optionally included in the design.

Similarly, the number of sensing electrode connectors 406B can vary depending upon the type of monitoring performed by the electrode node 400. For example, the electrode node 400 can include two sensing electrode connectors 406B, thereby providing for a single lead (e.g., lead I RA-LA as described above). In another example, the electrode node 400 can include three sensing electrode connectors 406B, thereby providing for three leads (e.g., lead I RA-LA, lead II RA-LL, and lead III LA-LL). In other examples, the electrode node 400 can include four or more sensing electrode connectors 406B. In such examples, the sensing electrode node connectors 406B may be organized and labelled such that alternative numbers of sensing electrodes can be used. For example, the electrode node 400 can include six sensing electrode node connectors 406B labelled 1-6. For a three lead monitoring device (including three sensing electrodes), sensing electrode connectors 406B numbers 1, 2, and 3 may be used.

As further shown in FIG. 4A, the electrode node 400 can include signal preprocessing circuitry 410. The signal preprocessing circuitry 410 can be operably connected to the sensing electrode connectors 406B and can be configured to receive at least one raw physiological signal from the sensing electrodes. The signal preprocessing circuitry 410 can be further configured to produce a primary physiological signal as well as a secondary physiological signal. In certain implementations, the primary physiological signal and the secondary physiological signal may be substantially the same as the raw physiological signal. In certain implementations, the raw physiological signal can include a plurality of raw physiological signals. For example, the raw physiological signals can include multiple raw signals leads for the patient.

In some examples, the signal preprocessing circuitry 410 can include a signal splitter configured to produce the primary and second physiological signals. In some implementations, the signal preprocessing circuitry 410 can further include an amplifier configured to amplify the primary and second physiological signals to account for any amplitude and/or power loss as a result of the dividing of the raw physiological signal. In some example, the signal preprocessing circuitry 410 can be further configured to perform additional preprocessing such as noise reduction, frequency filtering, signal conversion, and other similar signal processing.

FIG. 5A illustrates a sample circuit diagram for various components as shown in FIG. 4A, including signal preprocessing 410. As shown in FIG. 5A, in a particular example, inputs from two sensors can be directed to the signal preprocessing circuitry 410. For example, the input signals from each sensor in Lead I signal pair RA and LA can be directed to signal preprocessing circuitry 410. Each of input signals LA and RA can be split and directed to high impedance buffer amplifiers 502 and 504 respectively. Buffer amplifiers, such as those shown in FIG. 5A, are configured to transfer a voltage from a first circuit (having a high impedance level) to a second circuit having a low impedance level (as compared to the first circuit). To prevent the second circuit from loading the first circuit and interfering with its operation, the buffer amplifier is configured to have a relatively high impedance as compared to the first circuit. For example, the buffer amplifier can have an impedance 100 times, 1,000 times, or 10,000 times as high as the first circuit impedance, thereby preventing interference from the second circuit.

Returning again to FIG. 4A, first signal conditioning circuitry 415 can further condition the primary physiological signal. For example, the first signal conditioning circuitry 415 can perform noise filtering, signal amplification, analog to digital conversion, phase shifting, and other similar signal processing. A primary monitoring and/or treatment device 420 can receive the conditioned primary physiological signal and monitor one or more parameters for the patient. For example, the primary monitoring and/or treatment device 420 can be configured to monitor the patient for a cardiac event such as VT/VF occurrences. In certain implementations where the electrode node 400 and primary monitoring and/or treatment device are integrated into a treatment device such as a wearable defibrillator, the primary monitoring and/or treatment device can be further configured to provide one or more therapy pulses to the patient via one or more therapy electrodes operably connected to the therapy electrode connector 406A.

Referring back briefly to FIG. 5A input signals RA and LA can be directed from signal preprocessing circuitry 410 to first signal conditioning circuitry 415. The input signals can be divided and directed to a differential amplifier 506 and falloff signal processing 510. As noted above, a falloff signal can be broadcast into the patient's body to detect for whether the electrode has lost contact with the patient's skin or is otherwise compromised. A differential amplifier such as differential amplifier 506 can be included in first signal conditioning circuitry 415 to remove the falloff signal and other unwanted signals from the RA and LA inputs. A differential amplifier is configured to amplify the difference between two input voltages while suppressing any common mode signal or voltage common to the two inputs. As the falloff signal is common to both the RA and LA inputs, the differential amplifier 506 can remove this signal and output a signal proportional to the difference between the two inputs for further processing. For example, the output can be further processed by filtering circuitry 508. For example, for processing ECG signals, signals such high frequency signals and DC voltages may not be relevant for ECG measurement. As such, filtering circuitry 508 can include, for example, a low pass filter configured to pass any signals under a specific frequency (e.g., filtering any signal above a band of interest such as any signal above 200 Hz for diagnostic ECG signals) and/or a band-pass filter configured to pass a voltage between two frequencies (e.g., any signal between 40 Hz and 200 Hz). However, it should be noted that a low-pass filter and a band-pass filter are provided by way of example only. In some examples, a low pass filter, a notch filter, a high-pass filter, a block DC filter, and combinations thereof can be included in first signal conditioning circuitry 415 to implement the functionality thereof.

In certain implementations, the first signal conditioning circuitry 415 can include falloff signal processing circuitry 510. The falloff signal processing circuitry 510 can include circuitry components for conditioning the falloff signal for further processing by a monitoring device. For example, the falloff signal processing circuitry 510 can include circuitry components for amplifying the falloff signal including, for example, a differential amplifier, one or more bandpass filters, block filters, and other similar conditioning circuitry components.

Returning again to FIG. 4A, second signal conditioning circuitry 425 can further condition the secondary physiological signal. For example, the second signal conditioning circuitry 425 can perform noise filtering, signal amplification, analog to digital conversion, phase shifting, and other similar signal processing. The second signal conditioning circuitry 425 can provide the second conditioned physiological signal to telemetry circuitry 430.

Referring briefly back to FIG. 5A, input signals RA and LA can be directed from buffer amplifiers 502 and 504 to second signal conditioning circuitry 425. The input signals can be directed to a differential amplifier 512. Similar to differential amplifier 506, the differential amplifier 512 can be included in first signal conditioning circuitry 425 to remove the falloff signal from the RA and LA inputs. The differential amplifier 512 can remove the falloff signal and output a signal proportional to the difference between the two inputs for further processing. For example, the output can be further processed by filtering circuitry 514. For example, for processing ECG signals, signals such high frequency signals and DC voltages may not be relevant for ECG measurement. As such, filtering circuitry 514 can include, for example, a low pass filter configured to pass any signals under a specific frequency (e.g., any signal under 200 Hz) and/or a band-pass filter configured to pass a voltage between two frequencies (e.g., any signal between 40 Hz and 200 Hz). However, it should be noted that a low-pass filter and a band-pass filter are provided by way of example only. In some examples, a low pass filter, a notch filter, a high-pass filter, a block DC filter, and combinations thereof can be included in second signal conditioning circuitry 425 to implement the functionality thereof.

The circuitry as shown in FIG. 5A is provided by way of example only. As shown in FIG. 5A, the circuitry is configured to process two input signals received from individual sensors on a patient's body, in this example sensors RA and LA. As shown in FIG. 5B, similar circuitry can be included in, for example, electrode node 400 for processing input signals representing two leads, e.g., a front-back lead (FB) and a side-side (SS) lead where each lead can be derived from at least two ECG sensors on the patient's body.

As shown in FIG. 5B, input signals FB and SS can be directed to signal preprocessing circuitry 410. Each of input signals LA and RA can be split and directed to high impedance buffer amplifiers 522 and 524 respectively. The input signals FB and SS can be directed from signal preprocessing circuitry 410 to first signal conditioning circuitry 415. The input signals can be divided and directed to a differential amplifier 526 and falloff signal processing 530. As noted above, a falloff signal can be broadcast into the patient's body to detect for whether the electrode has lost contact with the patient's skin or is otherwise compromised. A differential amplifier such as differential amplifier 526 can be included in first signal conditioning circuitry 415 to remove the falloff signal from the FB and SS inputs. In some examples, the output can be further processed by filtering circuitry 528. For example, for processing ECG signals, signals such high frequency signals and DC voltages may not be relevant for ECG measurement. As such, filtering circuitry 528 can include, for example, a low pass filter configured to pass any signals under a specific frequency (e.g., any signal under 200 Hz) and/or a band-pass filter configured to pass a voltage between two frequencies (e.g., any signal between 40 Hz and 200 Hz). However, it should be noted that a low-pass filter and a band-pass filter are provided by way of example only. Any combination of a low-pass filter, band-pass filter, high-pass filter, or notch filter can be used within filtering circuitry 528 to implement the functionality thereof.

In certain implementations, the first signal conditioning circuitry 415 can include falloff signal processing circuitry 530. The falloff signal processing circuitry 510 can include circuitry components for conditioning the falloff signal for further processing by a monitoring device. For example, the falloff signal processing circuitry 510 can include circuitry components for amplifying the falloff signal including, for example, a differential amplifier, one or more bandpass filters, block filters, and other similar conditioning circuitry components.

As further shown in FIG. 5B, input signals FB and SS can be directed from buffer amplifiers 522 and 524 to second signal conditioning circuitry 425. Rather than direct the input signals to a differential amplifier as shown in FIG. 5A, the individual lead signals FB and SS can be processed individually prior to output to the telemetry circuitry. For example, each of input signals FB and SS can be further processed by filtering circuitry 532A and 532B. In certain implementations, filtering circuitry 532A and 532B can include, for example, a low pass filter configured to pass any signals under a specific frequency (e.g., any signal under 800 Hz) and/or a notch filter configured to pass a voltage between two frequencies (e.g., any signal between 20 Hz and 300 Hz). However, it should be noted that a low-pass filter and a notch filter are provided by way of example only. In some examples, a low pass filter, a notch filter, a high-pass filter, a block DC filter, and combinations thereof can be included in second signal conditioning circuitry 425.

Figure 5C:
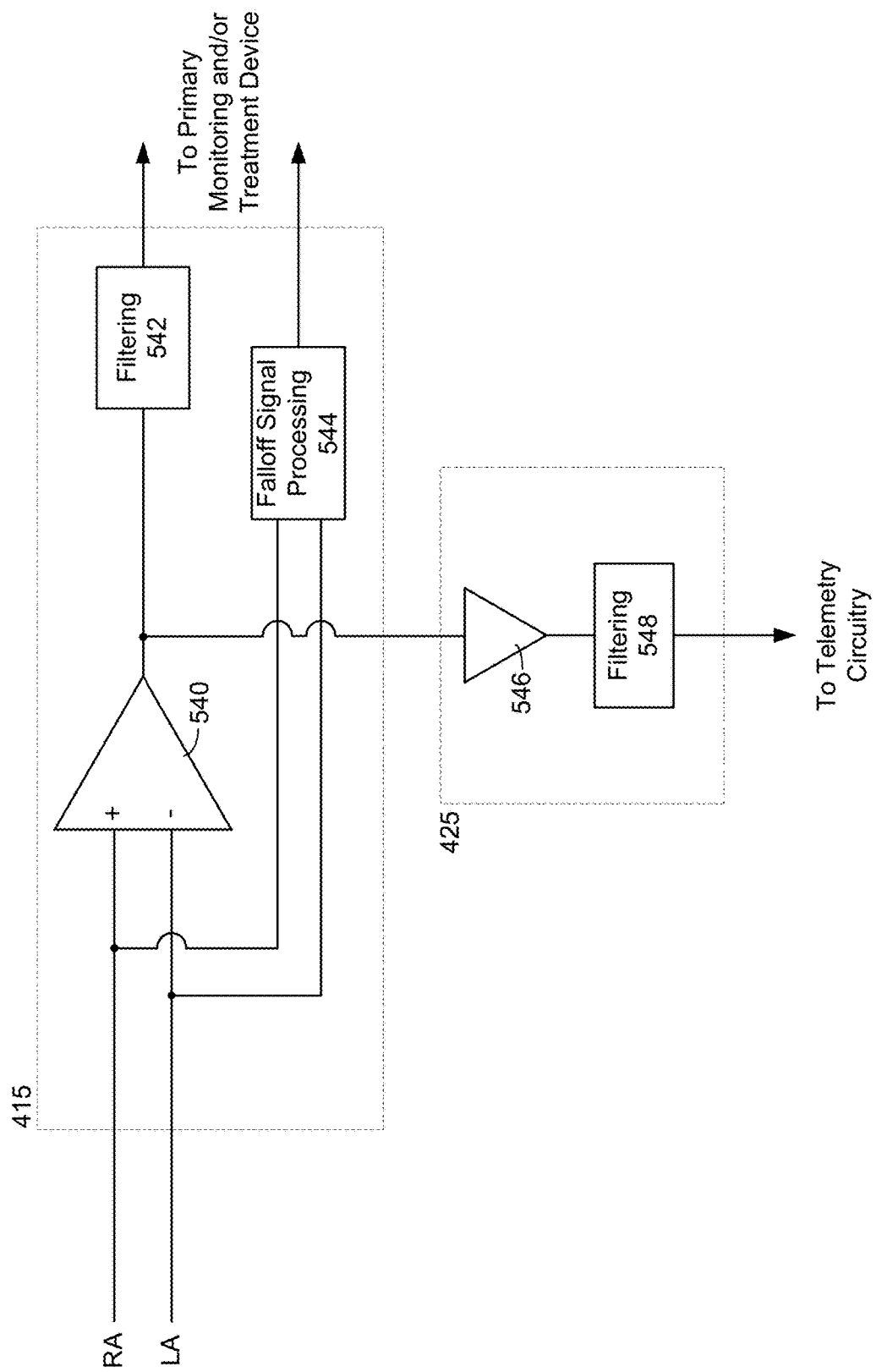
FIG. 5C depicts an alternate sample circuitry diagram for an electrode node such as the node shown in FIG. 4A, in accordance with an example of the present disclosure.

It should be noted that the circuits as shown in FIGS. 5A and 5B are provided by way of example only. In certain implementations, the number of components in the electrode node 400 can be reduced. For example, as shown in FIG. 5C, the signal preprocessing circuitry 410 can be reduced or eliminated from the electrode node 400. In such an arrangement, input signals RA and LA can be directed from, for example, ECG electrodes to the first signal conditioning circuitry 415. The input signals can be divided and directed to a differential amplifier 540 and falloff signal processing 544. As noted above, the differential amplifier 540 can be included in first signal conditioning circuitry 415 to remove the falloff signal and other unwanted signals from the RA and LA inputs. The output of the differential amplifier 540 can be further processed by filtering circuitry 542. In some examples, filtering circuitry 542 can include, for example, a low pass filter configured to pass any signals under a specific frequency (e.g., filtering any signal above a band of interest such as any signal above 200 Hz for diagnostic ECG signals) and/or a band-pass filter configured to pass a voltage between two frequencies (e.g., any signal between 40 Hz and 200 Hz). However, it should be noted that a low-pass filter and a band-pass filter are provided by way of example only. In some examples, a low pass filter, a notch filter, a high-pass filter, a block DC filter, and combinations thereof can be included in first signal conditioning circuitry 415 to implement the functionality thereof.

In certain implementations, the first signal conditioning circuitry 415 as shown in FIG. 5C can include falloff signal processing circuitry 544. The falloff signal processing circuitry 544 can include circuitry components for conditioning the falloff signal for further processing by a monitoring device. For example, the falloff signal processing circuitry 544 can include circuitry components for amplifying the falloff signal including, for example, a differential amplifier, one or more bandpass filters, block filters, and other similar conditioning circuitry components.

As further shown in FIG. 5C, the output of the differential amplifier 540 can be split and a copy of the signal can be directed to the second signal conditioning circuitry 425. For example, the output of the differential amplifier 540 can be directed to a high impedance buffer amplifier 546. To prevent the second circuit from loading the first circuit and interfering with its operation, the buffer amplifier 546 can be configured to have a relatively high impedance as compared to the first circuit. For example, the buffer amplifier 546 can have an impedance 100 times, 1,000 times, or 10,000 times as high as the first circuit impedance, thereby preventing interference from the second circuit.

The output of the buffer amplifier 546 can be further processed by, for example, filtering circuitry 548. In certain implementations, filtering circuitry 548 can include, for example, a low pass filter configured to pass any signals under a specific frequency (e.g., any signal under 200 Hz) and/or a band-pass filter configured to pass a voltage between two frequencies (e.g., any signal between 40 Hz and 200 Hz). The output of the filtering circuitry 548 can be directed to the telemetry circuitry for further processing.

Returning again to FIG. 4A, the telemetry circuitry 430 can be configured to model or condition expected telemetry signals for the patient. The telemetry circuitry 430 can be operably connected to a set of telemetry connectors 435 that can be used to provide the telemetry signals to one or more secondary monitoring devices such as a three lead ECG monitoring device. In certain implementations, the number of output telemetry signals is equal to the number of detected raw physiological signals. For example, if the raw physiological signal includes three lead signals, the output telemetry signals would include three output signals.

In certain implementations, the telemetry circuitry 430 can be operably connected to the primary monitoring and/or treatment device 420. In such an example, the telemetry circuitry 430 may be configured to receive an input signal from the primary monitoring and/or treatment device 420. In certain implementations, the input signal can provide an indication that the primary monitoring and/or treatment device 420 is preparing to provide a therapy pulse and the telemetry circuitry 430 should disconnect the secondary monitoring system to prevent damage to the secondary monitoring system as a result of the therapy pulse.

In other implementations, the input signal can provide an indication of one or more events that the primary monitoring and/or treatment device 420 has detected. For example, if the primary monitoring and/or treatment device 420 detects that the patient is experiencing an arrhythmia condition such as VT or VF, the input signal can instruct the telemetry circuitry 430 to output one or more output signals including an indication of the arrhythmia event to the secondary monitoring device. Similarly, if the primary monitoring and/or treatment device 420 detects that the patient is experiencing asystole, the input signal can instruct the telemetry circuitry 430 to output, for example, one or more output signals including an indication of an asystole event.

In some implementations, the primary monitoring and/or treatment device 420 can be configured to update the input signal if the primary monitoring and/or treatment device is detecting a high level of noise or a particular amount of noise for an extended period of time. For example, if the primary monitoring and/or treatment device 420 detects a signal amplitude above a particular threshold, the primary monitoring and/or treatment device can provide an indication via the input signal that there is a high level of noise. Similarly, if the primary monitoring and/or treatment device 420 detects a signal about a particular threshold for a period of time (e.g., ten seconds), the primary monitoring and/or treatment device can provide an indication via the input signal that there is an extended period of noise.

In some implementations, as noted above, various devices such as wearable defibrillators monitor for a falloff event. A falloff event is when one or more of the therapy electrodes and/or sensing electrodes disengage from the patient's skin. In some examples, a falloff event is detected by a monitoring device such as the primary monitoring and/or treatment device 420. In order to detect a falloff event, the primary monitoring and/or treatment device 420 uses one of the therapy electrodes or the sensing electrodes to transmitted a low frequency signal into the patient's body. The primary monitoring and/or treatment device 420 can then monitor each of the other electrodes to determine if those electrodes are detecting the transmitted signal. If one of the other electrodes does not detect the transmitted signal, the primary monitoring and/or treatment device 420 can determine that it is likely that the electrode has experienced a falloff event. If none of the other electrodes can detect the transmitted signal, the primary monitoring and/or treatment device 420 can determine that the electrode transmitting the signal has experienced a falloff event. In some examples, the primary monitoring and/or treatment device 420 can perform redundancy falloff detection by using another electrode to transmit the falloff signal to confirm a suspected falloff event.

Rather than merely have the secondary monitoring device output an emergency signal as a result of the falloff event, the primary monitoring and/or treatment device 420 can be configured to provide an input signal to the telemetry circuitry 430 instructing the telemetry circuitry to output a falloff event indication to the secondary monitoring system.

Table 1 shown below provides example input signals that can be relayed from the primary monitoring and/or treatment device 420 in accordance within some of the implementations described herein.

TABLE 1

| Input signal to telemetry circuit | Patient status | Primary device status | Telemetry circuit action |
| --- | --- | --- | --- |
| xTE_Pulse | In VT/VF condition | Preparing to deliver therapeutic defibrillation pulse(s) Deliver defibrillation pulse(s) | Disconnect/showoff telemetry/physically disconnect secondary monitoring system |
| xPac_Pulse | In paceable condition (e.g., bradycardiac, tachycardiac) | Preparing to deliver pacing pulse(s) Deliver pulse(s) | Disconnect/showoff telemetry/physically disconnect secondary monitoring system |
| xAsys_Pac_Pulse | Asystole | Preparing to deliver pacing pulse(s) Deliver pulse(s) | Indicate patient status to secondary monitoring system asystole condition OR Disconnect/shut off telemetry/ |

TABLE 1-continued

| Input signal to telemetry circuit | Patient status | Primary device status | Telemetry circuit action |
|---|---|---|---|
| | | | physically disconnection secondary monitoring system |
| xNoise_Detected | Unknown - noise detected on electrodes | Attempting to re-acquire signal | Indicate noise status to secondary monitoring system if feature is available in secondary monitoring system OR Disconnect/shut off telemetry/ physically disconnection secondary monitoring system |
| xFallOff_Detected | Electrode fall off event detected | Alert to nurses and/or caregivers | Indicate noise status to secondary monitoring system if feature is available in secondary monitoring system OR Disconnect/shut off telemetry/ physically disconnection secondary monitoring system |
| xLow_Batt | Battery is low | Alert to nurses and/or caregivers Provide visual indication of low battery | Provide visual indication of low battery |

In certain implementations, the telemetry circuit can be configured to output a diagnostic signal to a predetermined, specific telemetry connector. For example, as shown in FIG. 4A, the telemetry circuit 430 can be configured to output a diagnostic signal to telemetry connector 435x. This diagnostic signal can be used to transmit the input signals as shown in TABLE 1 above, or other similar diagnostic information to a secondary monitoring device.

As noted above, the second ECG signal conditioning circuitry is configured to be electrically isolated from the first ECG signal conditioning circuitry. In this regard, in certain implementations, the electrode node 400 as shown in FIG. 4A can be configured to electrically isolate the primary monitoring and/or treatment device 420, the secondary monitoring system (e.g., connected to the telemetry connectors 435), and the patient from any environmental electrical signals and conditions, accidental discharges, mains current feedback, electrostatic discharge, and other similar environmental or device electrical or mechanical faults. Electrical isolation can be based on customary circuit design and standard industry specifications. For example, the circuitry as described herein can incorporate the electrical requirements as defined for medical devices and contained within International Electrotechnical Commission (IEC) standard 60601-1. For example, the circuitry as described herein can satisfy the isolation and insulation requirements for a type BF (body floating) or type CF (cardiac floating) medical device as defined by IEC 60606-1. In certain implementations, the circuitry as described herein can satisfy the isolation and insulation requirements for an ambulatory medical device as defined by particular standard IEC 60601-2-47, a particular standard typically taking precedence over a general standard such as IEC 60601-1.

For example, the circuitry as described herein can be designed to include isolation of components to prevent shock or accidental discharge for a surge rated at 4 KV as defined by IEC 60601-2-47. Similarly, the circuitry can include a minimum creepage distance of 8 mm and use double-type insulation for all conductive components as defined by IEC 60601-2-47. If, due to design factors, the minimum creepage distance cannot be maintained, the thickness of the insulation can be increased by for example, 1.6 times the required thickness.

Figure 4B:
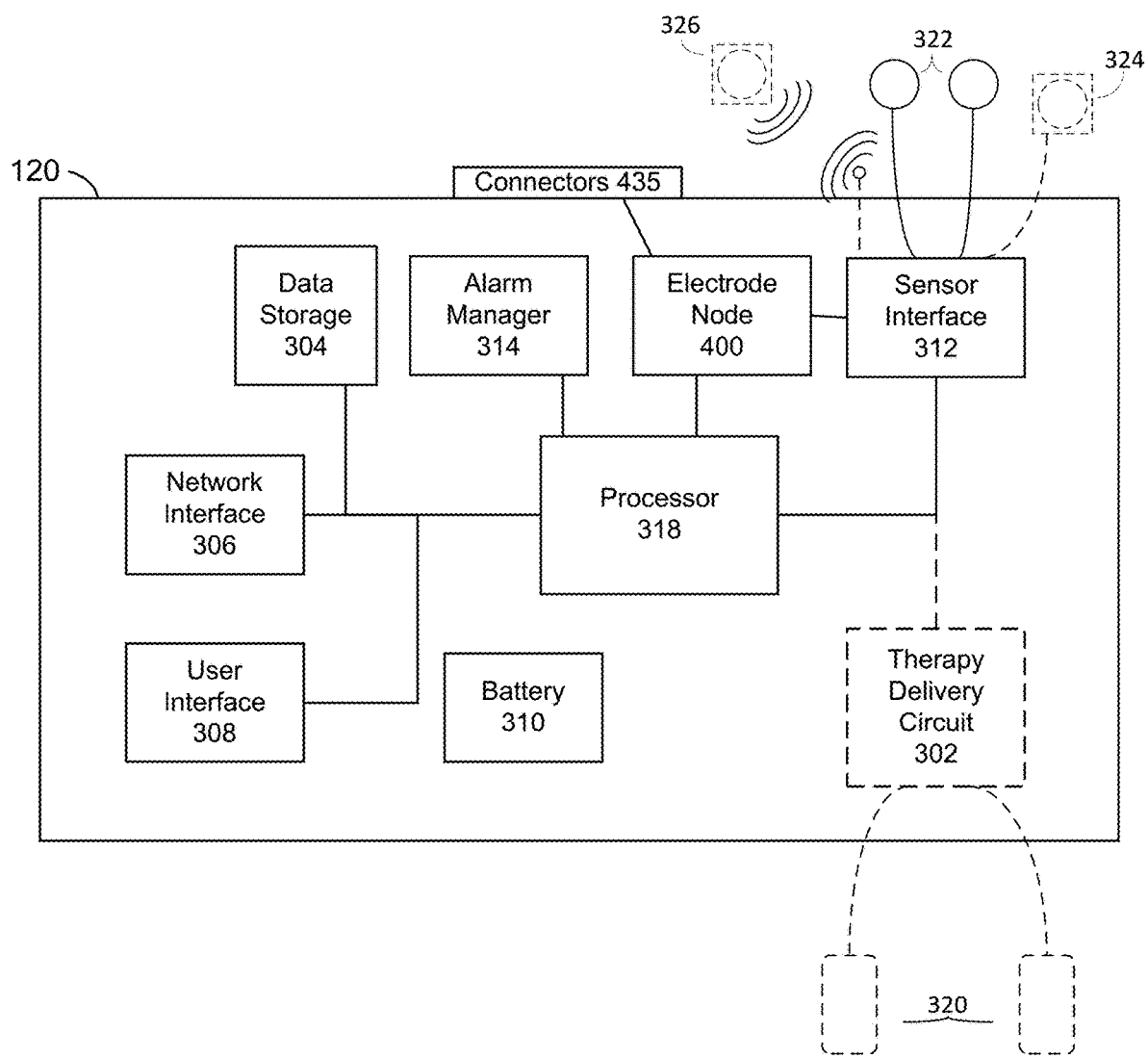
FIG. 4B depicts a schematic view of an electrode node integrated into a controller of a wearable medical device such as the controller illustrated in FIG. 3, in accordance with an example of the present disclosure.

In certain implementations, an electrode node such as electrode node 400 as shown in FIG. 4A can be integrated along with the primary monitoring and/or treatment device 420 into a single component such as controller 120 as described above. For example, as shown in FIG. 4B, controller 120 (as described above in the discussion of FIG. 3) can include electrode node 400. The electrode node 400 can be operably connected to the sensor interface 312 for receiving input signals from the various sensors places on the patient's body. In certain implementations, the electrode node 400 can also be operably connected to the processor 318. With respect to the electrode node 400, the processor 318 can be configured to function in a similar manner as described in connection with the primary monitoring and/or treatment device 420 of FIG. 4A. As further shown in FIG. 4B, the controller 120 can include telemetry connectors 435 for connecting the controller 120 of the primary monitoring and/or treatment device 420 directly to a secondary monitoring system (rather than via an external electrode node as in FIG. 4A).

Figure 6:
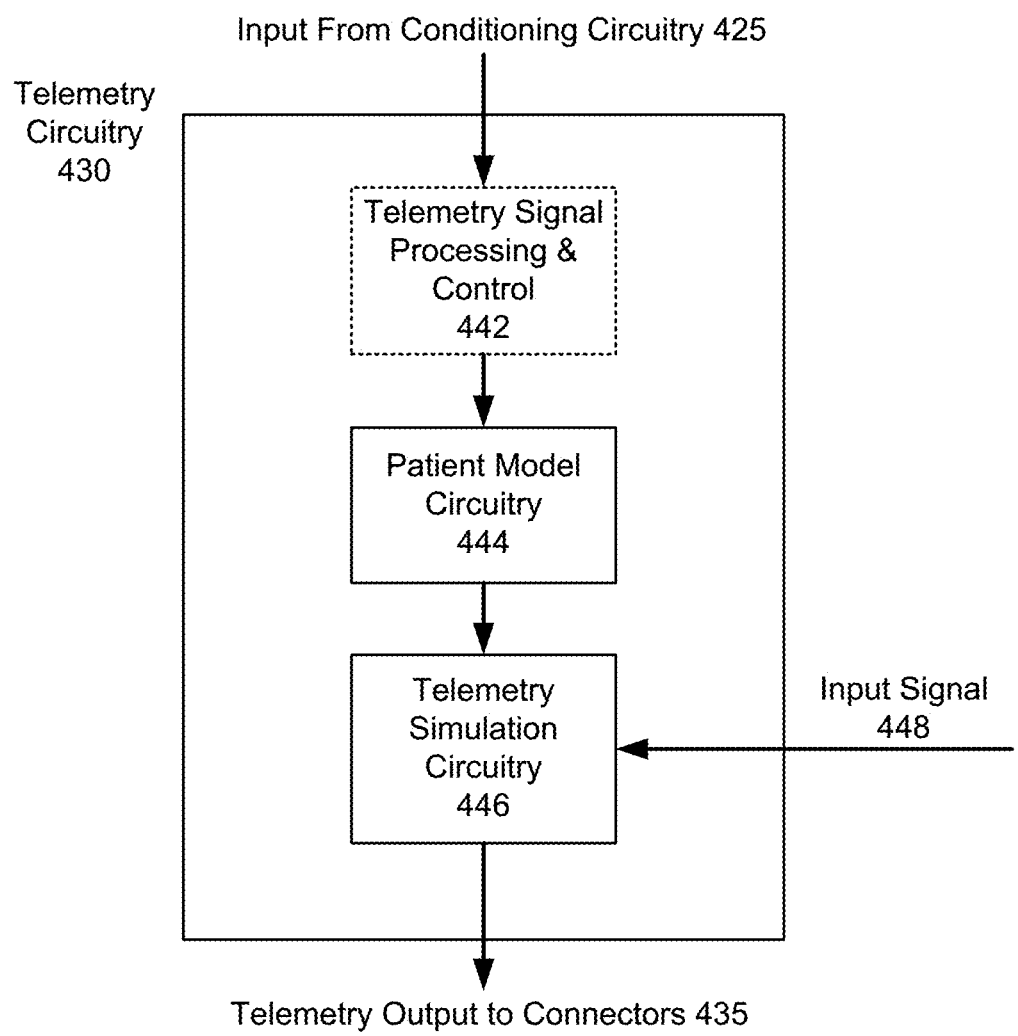
FIG. 6 depicts a schematic view of a telemetry modeling circuit, in accordance with an example of the present disclosure.

FIG. 6 shows a sample schematic for an example implementation of the telemetry circuitry 430. For example, the telemetry circuitry 430 can include telemetry signal processing and control circuitry 442. The processing and control circuitry 442 can be configured to function as a telemetry input configured to receive the conditioned secondary physiological signal from the second signal conditioning circuitry 425. The processing and control circuitry 442 can perform any additional processing on the conditioned secondary physiological signal and provide the conditioned secondary physiological signal to patient model circuitry 444. The patient model circuitry 444 can be implemented as a circuitry configured to model the electrical properties of a human body. For example, the patient model circuitry 444 can be implemented as a resistor network configured to receive the conditioned secondary physiological signal as an input, and output a modeled telemetry signal for the patient. Examples of the patient model circuitry 444 are shown in FIGS. 7A-7D and discussed in greater detail below.

As further shown in FIG. 6, telemetry simulation circuitry 446 can be configured to receive the output of the patient model circuitry 444. In an example, the telemetry simulation circuitry 446 may be relay switches that are configured to physically couple and decouple the electrical contacts of the electrode node 400 (e.g., contacts 435) from the secondary ECG processing system. In this regard, if an electrode falloff condition is sensed by the primary monitoring device, the primary monitoring device can transmit an input signal 448 to the telemetry simulation circuitry 446 to cause the relays to disconnect the secondary monitoring device from the electrode node 400. In implementations, additionally or alternatively, if a noise condition or other condition(s) that might adversely affect the ECG signals, is sensed by the primary monitoring device, the primary monitoring device can transmit an input signal 448 to the telemetry simulation circuitry 446 to cause the relays to disconnect the secondary monitoring device from the electrode node 400. Further, in certain examples, in the event of an arrhythmia condition, such as a shockable VT or VF condition, where the primary device might deliver therapeutic shocks, the primary device may transmit a signal via the input signal 448 line at an appropriate time (e.g., a few seconds prior to each therapeutic shock), to cause the relays to disconnect the secondary monitoring device.

The telemetry simulation circuitry 446 can be configured to provide one or more physiological signals based upon the output of the patient model circuitry 444 for output to a secondary monitoring device such as a three lead ECG monitoring device via telemetry connectors 435. In certain implementations, the telemetry simulation circuitry 446 can be further configured to receive the input signal from the primary monitoring and/or treatment device 420 and adjust the output accordingly. For example, if the input signal provides an indication that the primary monitoring and/or treatment device 420 has detected an electrode falloff event, the telemetry simulation circuitry 446 can be configured to output a falloff event signal to the secondary monitoring device, thereby overriding the output of the patient model circuitry 444 and simulating a falloff event to the secondary monitoring device.

Figure 7A:
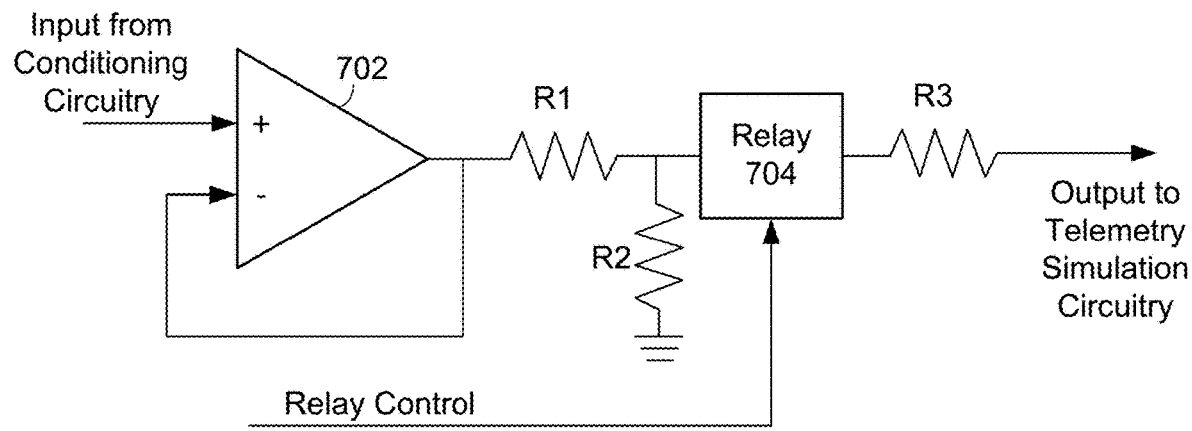
FIGS. 7A-7D depict sample patient model circuits, in accordance with examples of the present disclosure.
Figure 7B:
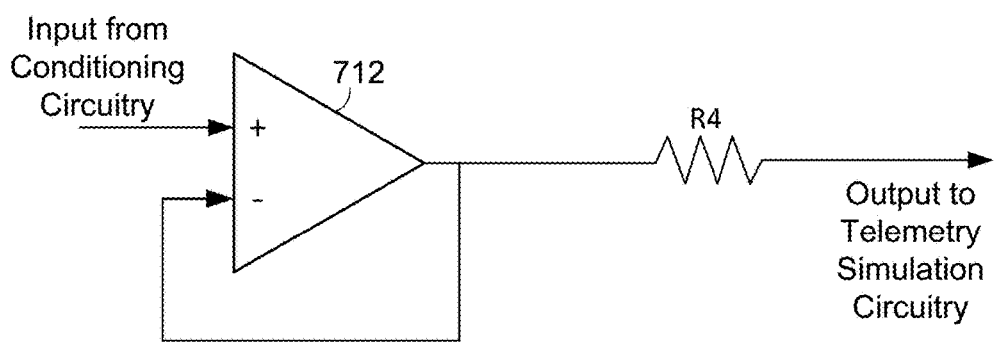

FIGS. 7A-7D illustrate example patient model circuitry and telemetry simulation circuitry such as patient model circuitry 444 and telemetry simulation circuitry 446 as described above. As noted above, for a three lead telemetry device, three electrode contact positions are typically used: RA, RL, and LL. Various differential voltage pairs of the electrode contact positions (RA, RL, and LL) are used to generate three limb leads: (LA-RA) for Lead I; (LL-RA) for lead II; and (LL-LA) for Lead III. In certain implementations, to properly model the three lead electrode contact signals for a three lead ECG monitoring device, each of the three sensor signals can be conditioned or otherwise modeled using patient model circuitry such as those shown in FIGS. 7A-7D. For example, circuitry 700 as shown in FIG. 7A can be used to model the RA and RL sensors (e.g., one instance of circuitry 700 for each sensor), and the circuitry 710 as shown in FIG. 7B can be used to model the LL sensor. Further, in FIGS. 7A and 7C, relays (704, 734a-c) are provided as part of the telemetry simulation circuitry 446. For example, an electrode falloff processing circuitry 730 can determine that a particular electrode (e.g. RA, LA as in FIG. 5A) or lead (e.g., FB or SS as in FIG. 5B) has an electrode falloff condition. In response, an associated relay 704, 734a-c for that particular lead may be opened so that the secondary device front end can also detect the electrode falloff on that lead.

As shown in FIG. 7A, circuitry 700 can include input from conditioning circuitry. For example, the input can be from secondary conditioning circuitry 425. Amplifier 702 can be configured to receive the input, amplify the input, and pass the amplified input through resistor R1. Following R1, the circuitry 700 can include a relay 704. As noted above, in the event of an electrode falloff event or other similar event, a primary monitoring device such as primary monitoring and/or treatment device 420 can provide an input signal including a relay control to open relay 704, thereby disconnecting the secondary monitoring device from the electrode node (e.g., electrode node 400). When the relay 704 is open, the amplified input can be directed through resistor R2. Otherwise, if the relay 704 is closed, the amplified input can be directed through resistor R3 and output to additional processing circuitry such as telemetry simulation circuitry 446. In this manner, the secondary device can operate based on substantially the same set of signals available to the primary device for a particular function such as lead off It should be noted that amplifier 702 is shown in circuitry 700 by way of example only. In some implementations, the amplifier 702 can be integrated into additional processing circuitry such as processing and control circuitry 442 as described above. Additionally, it should be noted that relay 704 is shown by way of example only as a way to physically disconnect the secondary monitoring device in the event of, for example, a therapeutic pulse being delivered to the patient.

As noted above, the circuitry 700 can be designed to mimic the electrical properties of the human body. As such, the values for R1, R2, and R3 can be chosen to most closely represent the internal impedance of the human body. In certain implementations, R1 can be configured to cancel any gain on the incoming signal. For example, R1 can be about 10 k$\Omega$. In other examples, R1 can be between about 5 k$\Omega$ to about 25 k$\Omega$. In some examples, R2 can be about 2 k$\Omega$. In other examples, R2 can be about 1 k$\Omega$ to about 5 k$\Omega$. In some examples, R3 can be about 1 k$\Omega$. In other examples, R3 can be about 100 $\Omega$ to about 2 k$\Omega$.

As shown in FIG. 7B, circuitry 710 can include input from conditioning circuitry. For example, the input can be from secondary conditioning circuitry 425. Amplifier 712 can be configured to receive the input, amplify the input, and pass the amplified input through resistor R4. In certain implementations, R4 can be about 100 Ω. In some examples, R4 can be about 50 Ω to about 500 Ω. Following R4, the amplified input can be output to additional processing circuitry such as telemetry simulation circuitry 446.

It should be noted that amplifier 712 is shown in circuitry 710 by way of example only. In some implementations, the amplifier 712 can be integrated into additional processing circuitry such as processing and control circuitry 442 as described above.

It should also be noted that circuitry 700 and circuitry 710 are shown as resistor networks by way of example only. In certain implementations, the patient model circuitry can include capacitors and/or a combination of resistors and capacitors.

Figure 7C:
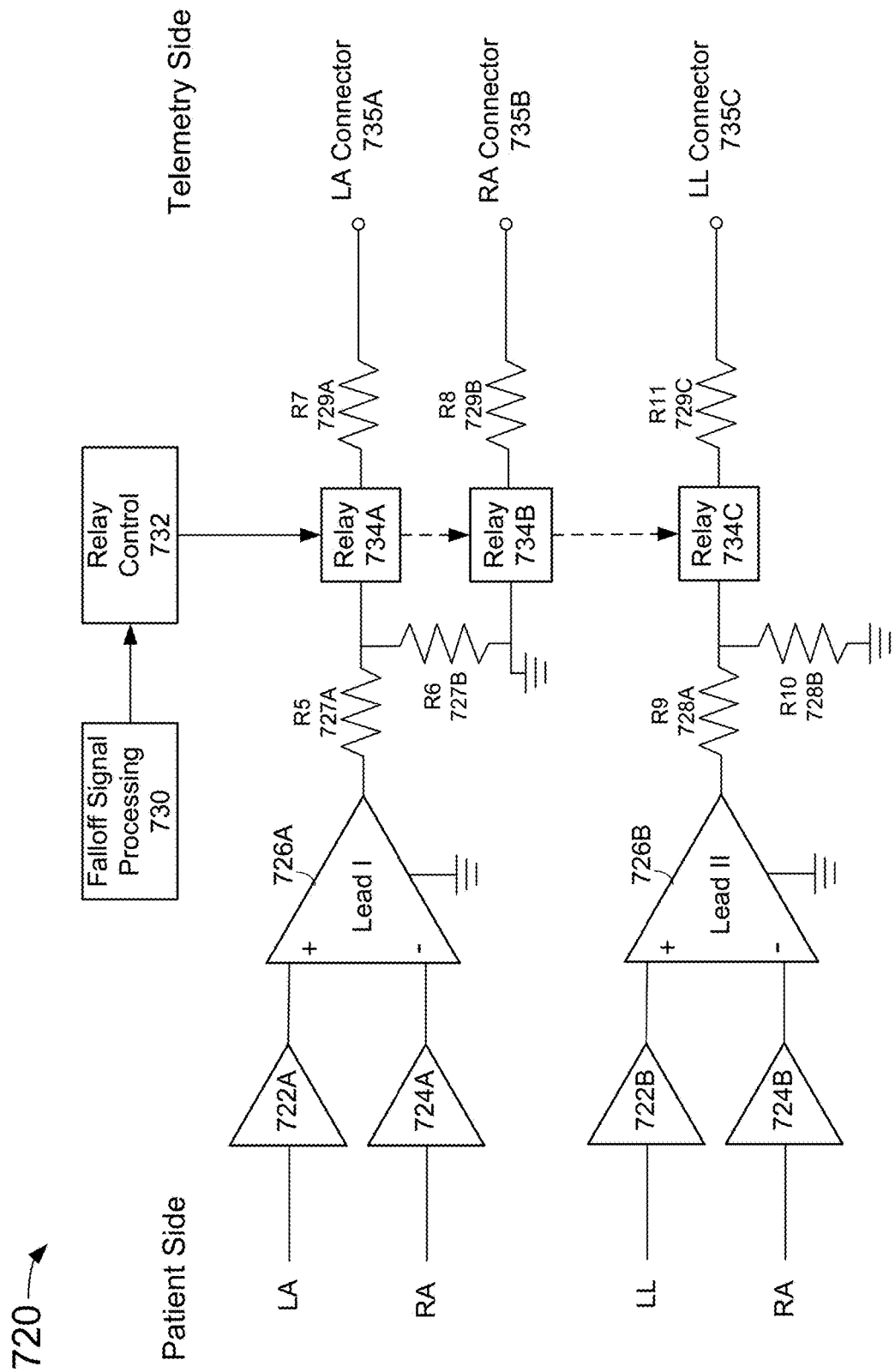

As shown in FIG. 7C, a patient model circuitry 720 (e.g., similar to patient model circuitry 444 as described above) can include buffer amplifiers 722A, 722B, 724A and 724B, differential amplifiers 726A and 726B, and resistors 727A, 727B, 728A, and 728B. Inputs to the amplifiers 722A, 722B, 724A, and 724B can be connected to the patient at the electrode contact positions, e.g. LL, LA, and RA. The differential amplifiers 726A and 726B can be configured to generate the ECG Lead vector, e.g. Lead I and Lead II. Resistors 727A, 727B, 728A, and 728B are configured to generate voltages at the secondary monitoring system connectors 735A-C such that the LA connector of the secondary monitoring system can be connected to 735A, the RA connector of the secondary monitoring system can be connected to 735B, the LL connector of the secondary monitoring system can be connected to 735C, and the appropriate ECG lead vectors, e.g. Lead I, II and III are generated by the secondary monitoring system. In certain implementations, circuitry 720 can further include resistors 729A, 729B, and 729C for further conditioning the signals for processing by the telemetry circuitry prior to outputting to connectors 735A-C.

As further shown in FIG. 7C, circuitry 720 can further include falloff signal processing circuitry 730 configured to process a falloff signal to determine whether one or more sensors have fallen off or otherwise lost contact with the patient as described above. The falloff signal processing circuitry 730 can be operably connected to relay control 732 which is connected to each of relays 734A, 734B, and 734C. Upon receiving a signal that one or more sensors have fallen off the patient or is otherwise compromised, the falloff signal processing circuitry 730 can provide an input to the relay control 732 to open a relay associated with the sensor that has fallen off, thereby providing an indication to the secondary monitoring system that one or more sensors of the primary device is compromised.

Figure 7D:
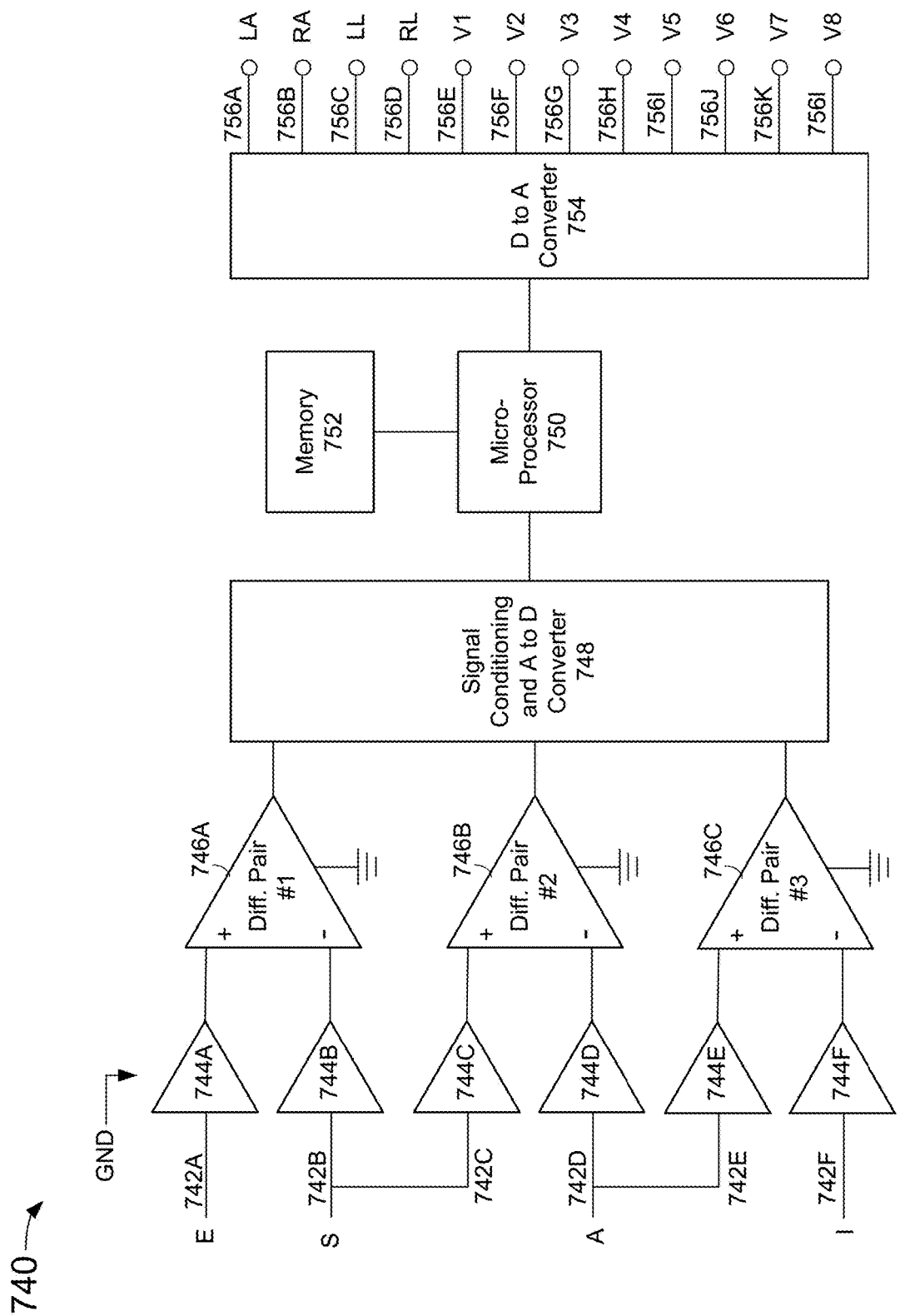

FIG. 7D illustrates an example patient model circuit that includes microprocessor-controlled digital signal processing. Input signals 742A-F can be input into one of buffer amplifiers 744A-F. The outputs of amplifiers 744A-F can be input, via differential amplifiers 746A-C, to signal conditioning circuitry 748 for processing and conversion from an analog to a digital waveform. For example, the signal conditioning and A-D converting circuitry 748 can include an ADAS1000 five electrode ECG analog front end (from Analog Devices, Norwood, Mass., USA). For example, the ADAS1000 can be in any of parts ADAS1000 and ADAS1000-2 (5 ECG electrodes including a right leg drive) and ADAS1000-1 (5 ECG electrodes). The digital waveform data can be stored in memory 752 and processed by the microprocessor 750. The microprocessor 750 can process the digital waveform and pass the processed signal to a digital to analog converter 754. The D-A converter can convert the digital output to one or more analog signals and output to one of output connectors 756A for processing by a secondary telemetry device.

In certain implementations, components from both FIGS. 7C and 7D can be implementing into the same circuitry. For example, the outputs of amplifiers 726A and 726B can be digitized by the A/D converter 748, stored in memory 752 by the microprocessor 750. The stored outputs can be retrieved by the microprocessor 750 from memory 752 to be output by the D/A converter 754 into resistor divider networks 727A/727B and 728A/728B and output via the telemetry simulation circuit (e.g. Relays #1-3 734A-C and resistors 729A-C) to the telemetry terminals 735A-735C.

In certain implementations, one or more of the telemetry side signals 756A-L can be derived from some combination of two or more patient side signals 742A-F. In other words, the patient side signals are a so-called reduced lead set, for example the EASI system developed by Dr. Gordon Dower. The advantages of deriving the twelve-lead ECG from the EASI system, for example, rather than recording it directly, include greater patient comfort and mobility, reduced artifact, and simpler lead placement of the primary device electrodes than placement of electrodes needed for a twelve-lead ECG system. Further, the primary medical device and/or electrode node lead placement can be based on a simpler ECG system than standard ECG systems, which includes relatively easy-to-locate anatomical landmarks. Such a reduced-lead system can allow for easier training of nurses, caregivers, and other in-hospital support personnel. The reduced-lead system also results in better reproducibility in electrode placement. Further, in reduced-lead systems such as the EASI system, an absence of midprecordial leads can provide better access to the patient's chest for other procedures, such as auscultation or echocardiographic examination. In addition, there are cost savings due to fewer electrodes and simpler electronics and a lower number of ECG channels of ECG acquisition.

The EASI method of obtaining a twelve-lead ECG requires only five electrodes (4 monitoring electrodes and a ground electrode). For example, as shown in FIG. 7D, circuitry 740 can include a ground input signal, an E input signal (742A), an S input signal (742B and 742C), an A input signal (744D and 744E), and an I input signal (744F).

For example, the electrode for the E input signal may be located at a level of the fifth on the lower sternum. For example, the electrode for the A input signal may be located in the left midaxillary line at a same level as the electrode for the E input signal. For example, the electrode for the S input signal may be located on the manubrium sterni. For example, the electrode for the I input signal may be located in the right midaxillary lines at a same level as the E electrode. For example, the ground electrode may be placed at any convenient location on the patient's body. A time-varying voltage, V, in an ECG lead in accordance with the EASI system is a solution of the following equation: $V=aV_{ES}+bV_{AS}cV_{AI}$. $V_{ES}$, $V_{AS}$, and $V_{AI}$ are the time-varying voltages of the ES electrode pair, AS electrode pair, and AI electrode pair. The coefficients a, b, and c are fixed coefficients appropriate to the lead being derived. For example, the coefficients can be selected to define a three-dimensional lead vector. In this manner, there can be a derived lead vector for each ECG lead in accordance with the twelve-lead ECG system. For example, the coefficients can be based on historical patient ECG information (e.g., using EASI-based ECG data from a cohort of around 1000 patients and comparing to the twelve-lead ECG system). For example, the coefficients may be based on a universal search method with a mean-squared distance as a metric for evaluating the resulting synthesis. In this method, the best combination of coefficients can result in a minimum mean-squared distance over all the available measurements.

Example coefficients for each of the twelve standard leads are shown Table 2 below:

TABLE 2

| Lead | ES | AS | AI |
| --- | --- | --- | --- |
| I | 0.026 | −0.174 | 0.701 |
| II | −0.002 | 1.098 | −0.763 |
| III | −0.028 | 1.272 | −1.464 |
| aVR | −0.012 | −0.462 | 0.031 |
| aVL | 0.027 | −0.723 | 1.082 |
| aVF | −0.015 | 1.185 | −1.114 |
| V1 | 0.641 | −0.391 | 0.080 |
| V2 | 1.229 | −1.050 | 1.021 |
| V3 | 0.947 | −0.539 | 0.987 |
| V4 | 0.525 | 0.004 | 0.841 |
| V5 | 0.179 | 0.278 | 0.630 |
| V6 | −0.043 | 0.431 | 0.213 |

For example, based on the above Table 2, $V_{Lead1}=0.026V_{ES}-0.174V_{AS}+0.701V_{AI}$. Additional example EASI coefficients based on a dataset involving 983 adult subjects are shown and described in, for example, Field et al., D. Q. Feild, C. L. Feldman, and B. M. Horáček, "Improved EASI Coefficients: Their Derivation, Values, and Performance," Journal of Electrocardiology, vol. 35 Suppl, pp. 23-33, 2002, which is incorporated by reference herein in its entirety.

Other reduced lead sets can be used such as the Frank Method described in, for example, Tomašgié et al, I. Tomašgié and R. Trobec, "Electrocardiographic Systems With Reduced Numbers of Leads—Synthesis of the 12-Lead ECG," in IEEE Reviews in Biomedical Engineering, vol. 7, pp. 126-142, 2014, which is incorporated by reference herein in its entirety. Thus, with a reduced number of leads on the patient's body, the telemetry simulation circuit can output more leads and more information, e.g. a standard 5-lead output, a twelve-lead output (as shown in FIG. 7D), even 15 or 18 leads to the secondary monitoring system, thereby reducing clutter on the patient's body during various clinical procedures, or providing more room on the patient's body for other sensors.

Figure 8:
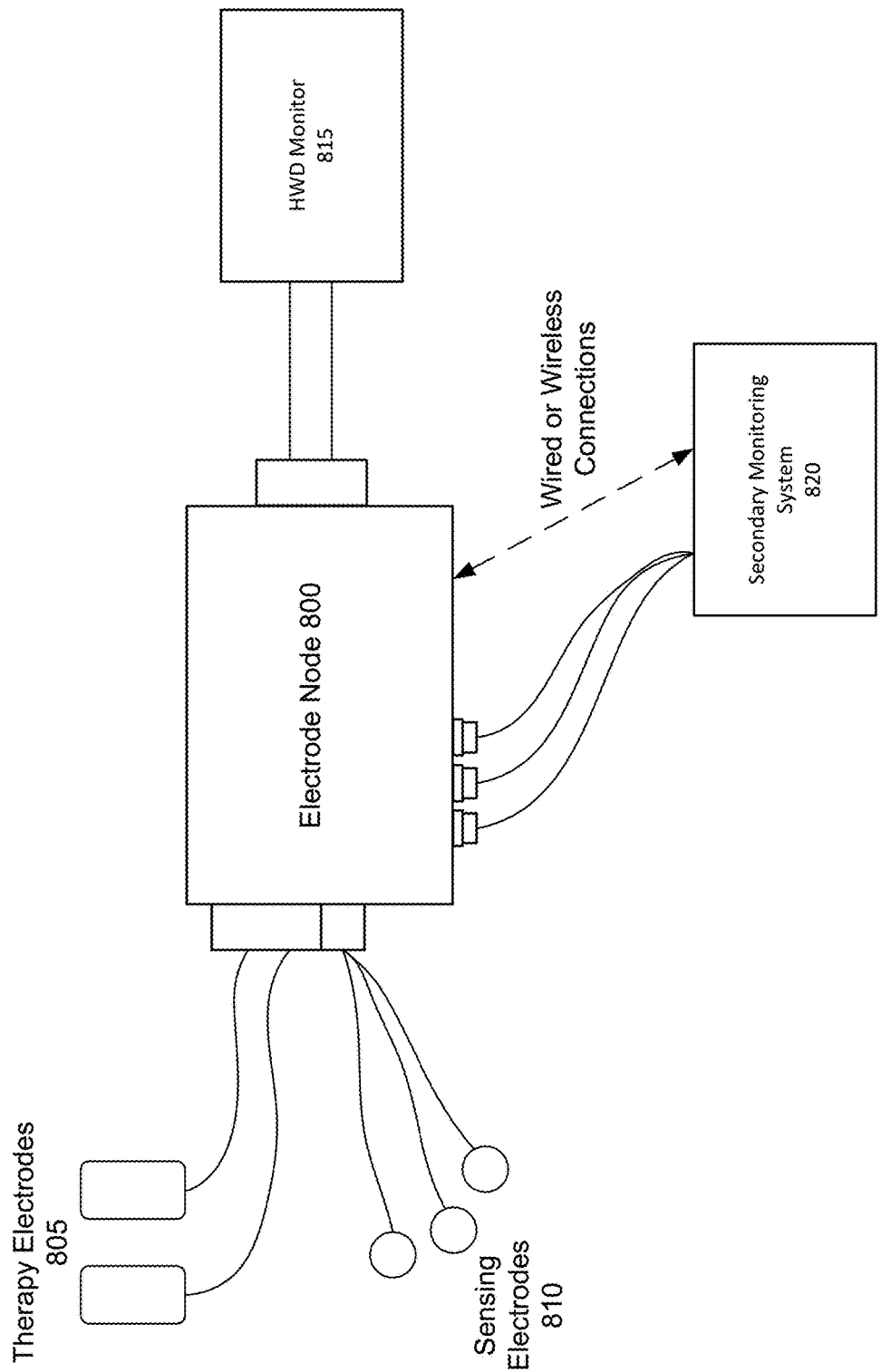
FIG. 8 depicts a schematic view of a system including a wearable medical device and a secondary monitoring system, in accordance with an example of the present disclosure.

FIG. 8 illustrates a schematic view of a system including a wearable medical device and a secondary monitoring system. For example, electrode node 800 can be integrated into a wearable treatment device such as a HWD. A set of therapy electrodes 805 can be operably connected to the electrode node 800 and configured to provide a therapeutic shock to a patient. A set of sensing electrodes 810 can also be operably connected to the electrode node 800 and configured to detect raw physiological signals from the patient.

As further shown in FIG. 8, a HWD monitor 815 can be operably connected to the electrode node 800. The HWD monitor 815 can be configured to monitor physiological signals for the patient and determine if the patient is experience, for example, a cardiac event. If the HWD monitor 815 detects a cardiac event, the HWD monitor can be configured to provide a therapeutic pulse to the patient via the therapy electrodes 805.

Additionally, as shown in FIG. 8, a secondary monitoring system 820 can be operably connected to the electrode node 800. As described above, the electrode node 800 can be configured to output telemetry signals for monitoring by the secondary monitoring system 820. For example, the secondary monitoring system 820 can be integrated as a bedside ECG monitoring device in a hospital environment.

It should be noted that the secondary monitoring system 820 can be connected to the electrode node 800 using a wired or wireless connection. For example, depending upon the functionality of the secondary monitoring system 820, the secondary monitoring system can connect to the electrode node 800 using a short range wireless communication protocol such as Bluetooth or another similar communication protocol. In certain implementations, if the secondary monitoring system 820 does not include wireless capabilities, a wireless adapter can be operably connected to the secondary monitoring system and configured to establish a wireless connection with the electrode node 800. Such a wireless arrangement can be used to limit the number of wires coming from the electrode node 800, thereby potentially increasing the mobility and comfort of the patient wearing the treatment device.

Figure 9:
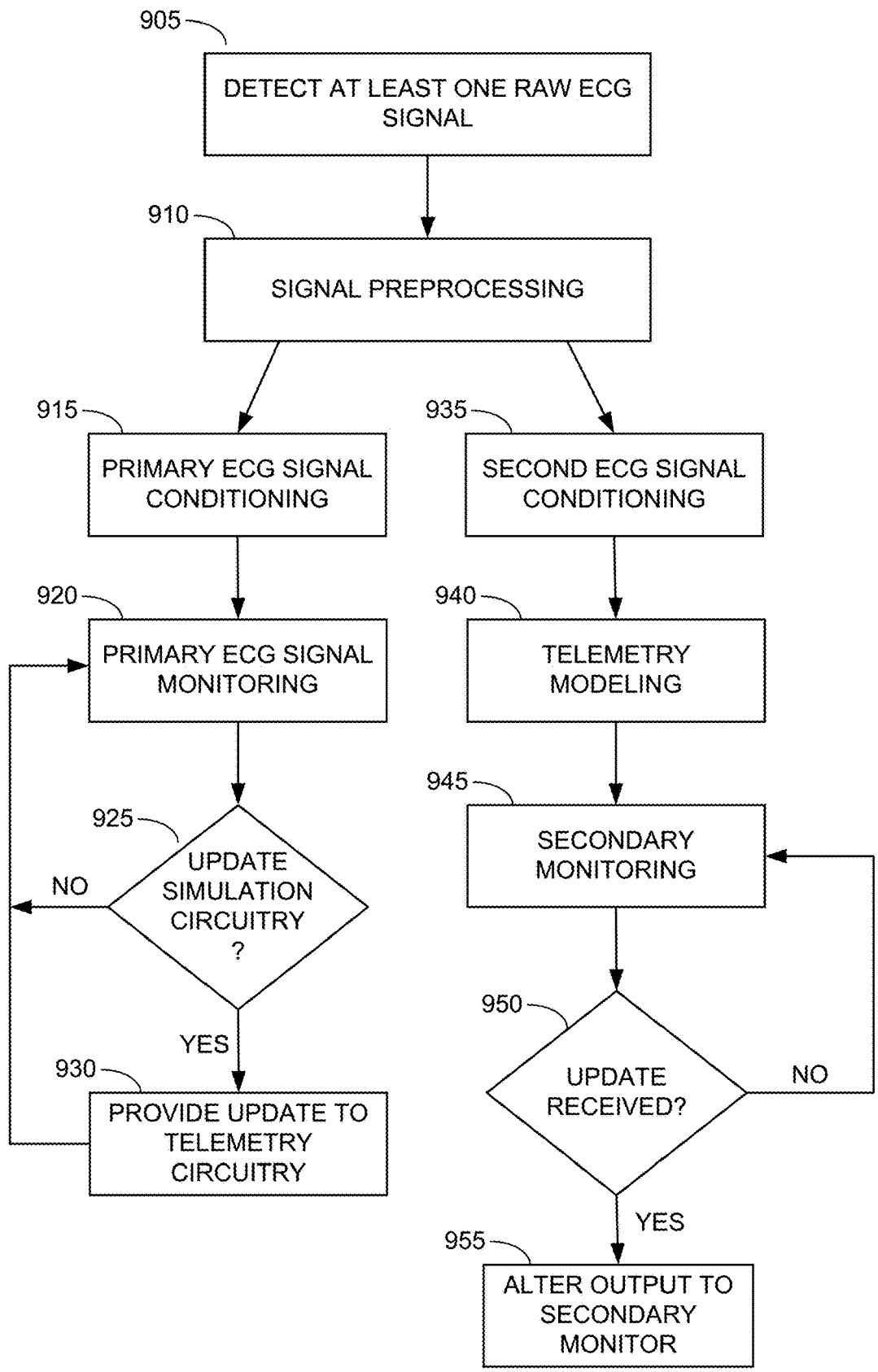
FIG. 9 depicts a sample flow diagram showing an example of a signal processing flow, in accordance with an example of the present disclosure.

FIG. 9 illustrates a sample flow diagram showing an example of a signal processing flow. As noted above, the techniques and teachings as disclosed herein can be used to monitor one or more physiological signals for a patient and to output telemetry signals for monitoring by a secondary monitoring device. The process as shown in FIG. 9 is directed to a specific implementation where the physiological signal is an ECG signal. The process can include detecting 905 at least one raw ECG signal. The at least one raw ECG signal can be preprocessed 910 to produce a primary ECG signal and a secondary ECG signal. The primary ECG signal can be conditioned 915. The conditioned signal can be monitored 920 by a primary monitoring device. The secondary ECG signal can also be conditioned 935. The conditioned signal can be modeled 940 by telemetry modeling circuitry and output as one or more output telemetry signals. The output telemetry signals can be monitored 945 by a secondary monitoring device.

As described above, the primary monitoring device can monitor the primary ECG signal for an abnormal event such as a falloff event, a cardiac event, or another similar event. As shown in FIG. 9, the primary monitoring device can determine 925 if the primary ECG signal indicates an abnormal event. If the primary monitoring device determines 925 there are no abnormal events, the primary monitoring device can continue to monitor 920 the primary ECG signal. If the primary monitoring device does determine 925 there is an abnormal event, the primary monitor can provide 930 an update (e.g., via the input signal as described above) to the telemetry circuitry.

As further shown in FIG. 9, the telemetry circuitry can determine 950 whether an update has been received from the primary monitoring device. If the telemetry circuitry determines 950 that there is no update, the secondary monitoring device can continue to monitor 945 the output telemetry signals. If the telemetry circuitry does determine 950 that there is an update, the telemetry circuitry can alter 955 the output to the secondary monitoring device, thereby providing an indication of the abnormal event to the secondary monitoring device.

As noted above, processing a raw ECG signal as described in the above discussion of FIG. 9 is provided by way of example only. The teachings as described herein can be directed to additional physiological signals as well. For example, as shown in FIG. 4A, the electrode node 400 can be operably connected to additional sensors such as acoustic sensors, oxygen sensors, and other similar sensors. Using these additional sensors, additional physiological signals such as cardio-acoustic signals, bio-acoustic signals, lung vibrations, pulse oxygen levels, thoracic fluid content, muscle oxygenation (based upon, for example, reflectance technology), and other physiological signals can be measured and, in certain implementations, provided to the secondary monitoring device. Similar, RF-based sensors such as fluid monitoring device can be used to collect additional physiological information such as heart wall motion information, tissue fluid levels, and continuous blood pressure values.

Use-Case Examples

In an example, a person may have a medical emergency in a location that requires emergency medical assistance from, for example, an ambulance or another similar type of emergency response crew. Depending upon the type of emergency, and the overall health of the patient, the medical responders may determine the patient is to be fitted with an ambulatory defibrillation device for transportation to a medical care facility. Conversely, the patient may already be wearing an ambulatory defibrillation device upon arrival of the emergency responders. In either case, the emergency responders may also want to monitor various other physiological signals for the patient that are not monitored or otherwise displayed by the ambulatory defibrillation device. In such an example, the emergency medical responders may operably connect a secondary monitoring device, such as an ECG monitoring device integrated into or stored within the ambulance, to an electrode node or other connection point on ambulatory defibrillation device. Thus, as opposed to placing an additional set of sensors on the patient, the emergency responders can gather additional physiological information for the patient using a single set of sensors, e.g., the sensing electrodes associated with the ambulatory defibrillation device. Thus, the functionality of the ambulatory defibrillation device is maintained along with the added functionality of the secondary monitoring device.

In another example, a patient may be prescribed a wearable treatment device such as a wearable defibrillator for an extended period of time (e.g., 30 days). A monitoring device integrated into the wearable treatment device can include outputs for attachment of, for example, an ECG monitoring device or another similar secondary monitoring device. During a visit to their doctor, the doctor can connect a secondary monitoring device to the patient's wearable treatment device to perform various functions. For example, the doctor can verify the functionality of the wearable treatment device. The doctor can also use any added functionality of the secondary monitoring device to do a more involved analysis of the patient. For example, the wearable treatment device may be configured to monitor a limited amount of information related to the patient such as heartrate from a measured ECG signal. However, the secondary monitoring device can be configured to determine additional information from the ECG signal for the patient that the doctor may want to monitor or verify.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. An electrocardiogram (ECG) signal processing system, comprising:
   a plurality of ECG sensing electrodes configured to be placed proximate to a patient's skin and detect at least one raw ECG signal lead of the patient; and
   an ECG node device comprising
      an ECG pre-processing circuitry operably connected to the plurality of ECG sensing electrodes and configured to
         receive the at least one raw ECG signal lead via the plurality of ECG sensing electrodes; and
         process the at least one raw ECG signal lead to produce a primary ECG signal lead and a secondary ECG signal lead split from the primary ECG signal lead such that the secondary ECG signal lead is substantially the same as the primary ECG signal lead;
      a first ECG signal conditioning circuitry configured to condition the primary ECG signal lead and provide the conditioned primary ECG signal lead to a primary ECG monitoring system;
      a second ECG signal conditioning circuitry configured to be electrically isolated from the first ECG signal conditioning circuitry and configured to condition the secondary ECG signal lead; and
      a telemetry circuitry electrically coupled to the second ECG signal conditioning circuitry, the telemetry circuitry comprising
         a telemetry input configured to receive the conditioned secondary ECG signal lead and at least one input from the primary ECG monitoring system;
         a telemetry simulation circuitry configured to simulate one or more ECG signal conditions of the patient based on the conditioned secondary ECG signal lead and the at least one input from the primary ECG monitoring system; and
         a plurality of telemetry output connectors configured to provide one or more output telemetry signals based on the simulated one or more ECG signal conditions of the patient to a secondary ECG processing system.

2. The ECG signal processing system of claim 1, wherein the telemetry simulation circuitry comprises one or more relays to disconnect the telemetry circuitry from the plurality of telemetry output connectors in response to the at least one input from the primary ECG monitoring system.

3. The ECG signal processing system of claim 2, wherein the at least one input from the primary ECG monitoring system comprises one or more of an electrode falloff condition, an indication of a noise condition, and an indication of an arrhythmia condition.

4. The ECG signal processing system of claim 1, wherein the at least one raw ECG signal lead comprises a plurality of raw ECG signal leads, and the telemetry circuitry is configured to provide a plurality of output telemetry signals corresponding to each one of the plurality of raw ECG signal leads of the patient.

5. The ECG signal processing system of claim 1, wherein the simulated one or more ECG signal conditions of the patient comprises an electrode falloff condition.

6. The ECG signal processing system of claim 1, wherein the second ECG signal conditioning circuitry is further configured to filter out one or more electrical signals applied to the patient by the primary ECG monitoring system.

7. The ECG signal processing system of claim 1, wherein the telemetry circuitry further comprises a patient model comprising a resistor network configured to model one or more electrical parameters of the patient.

8. The ECG signal processing system of claim 7, wherein the telemetry simulation circuitry is further configured to simulate the one or more ECG signal conditions by directing the conditioned secondary ECG signal lead through the resistor network.

9. The ECG signal processing system of claim 8, wherein the simulated one or more ECG signal conditions comprise a noise condition and an arrhythmia condition.

10. The ECG signal processing system of claim 1, wherein the telemetry circuitry is further configured to wirelessly provide the one or more output telemetry signals to the secondary ECG processing system.

11. The ECG signal processing system of claim 1, wherein conditioning the secondary ECG signal lead comprises at least one of performing noise filtering, performing signal amplification, and performing analog to digital conversion on the secondary ECG signal lead.

12. The ECG signal processing system of claim 1, further comprising one or more sensors configured to detect at least one of a cardio-vibrational signal, a pulmonary-vibrational signal, and a pulse oxygen level of the patient.

13. The ECG signal processing system of claim 1, wherein the secondary ECG processing system comprises one of a three ECG lead telemetry device, a six lead ECG monitoring device, and a twelve lead ECG monitoring device.

14. The ECG signal processing system of claim 1, further comprising at least two therapy electrodes configured to be placed proximate to the patient's skin and further configured to deliver at least one therapeutic shock to the patient.

15. The ECG signal processing system of claim 1, wherein the telemetry circuitry is isolated to protect the patient from environmental electrical noise.

16. An ambulatory medical device, comprising:
a plurality of electrocardiogram (ECG) sensing electrodes configured to be in substantially continuous contact with a patient's skin over an extended period of time and detect at least one raw ECG signal lead of the patient;
an ECG monitoring circuitry coupled to the plurality of ECG sensing electrodes and configured to determine one or more cardiac arrhythmia conditions in the patient;
an ECG pre-processing circuitry operably connected to the plurality of ECG sensing electrodes and configured to
receive the at least one raw ECG signal lead via the plurality of ECG sensing electrodes; and
process the at least one raw ECG signal lead to produce a primary ECG signal lead and a secondary ECG signal lead split from the primary ECG signal lead such that the secondary ECG signal lead is substantially the same as the primary ECG signal lead;
a first ECG signal conditioning circuitry configured to condition the primary ECG signal lead and provide the conditioned primary ECG signal lead to the ECG monitoring circuitry, the ECG monitoring circuitry being configured to determine the one or more cardiac arrhythmia conditions in the patient based on the conditioned primary ECG signal lead;
a second ECG signal conditioning circuitry configured to be electrically isolated from the primary ECG signal conditioning circuitry and configured to condition the secondary ECG signal lead; and
a telemetry circuitry electrically coupled to the second ECG signal conditioning circuitry, the telemetry circuitry comprising telemetry output connectors configured to provide one or more output telemetry signals based on the conditioned secondary ECG signal lead to secondary ECG monitoring circuitry.

17. The ambulatory medical device of claim 16, wherein the telemetry circuitry further comprises:
a telemetry input configured to receive the conditioned secondary ECG signal lead and at least one input from the ECG monitoring circuitry; and
telemetry simulation circuitry configured to simulate one or more ECG signal conditions of the patient based on the conditioned secondary ECG signal lead and the at least one input from the ECG monitoring circuitry.

18. The ambulatory medical device of claim 17, wherein the telemetry simulation circuitry further comprises one or more relays to disconnect the telemetry circuitry from the plurality of telemetry output connectors in response to the at least one input from the ECG monitoring circuitry.

19. The ambulatory medical device of claim 16, wherein the at least one raw ECG signal lead comprises a plurality of raw ECG signal leads, and the telemetry circuity is configured to provide a plurality of output telemetry signals corresponding to each one of the plurality of raw ECG signal leads of the patient.

20. The ambulatory medical device of claim 16, wherein the second ECG conditioning circuitry is further configured to filter out one or more electrical signals applied to the patient by the ECG monitoring circuitry.

21. The ambulatory medical device of claim 16, wherein the telemetry circuitry further comprises a patient model comprising a resistor network configured to model one or more electrical parameters of the patient.

22. The ambulatory medical device of claim 21, wherein the telemetry circuitry is further configured to simulate the one or more ECG signal conditions by directing the conditioned secondary ECG signal lead through the resistor network.

23. The ambulatory medical device of claim 22, wherein the simulated one or more ECG signal conditions comprise a noise condition and an arrhythmia condition.

24. The ambulatory medical device of claim 16, wherein the telemetry circuitry is further configured to wirelessly provide the one or more output telemetry signals to the secondary ECG monitoring circuitry.

25. The ambulatory medical device of claim 16, wherein conditioning the secondary ECG signal lead comprises at least one of performing noise filtering, performing signal amplification, and performing analog to digital conversion on the secondary ECG signal lead.

26. The ambulatory medical device of claim 16, further comprising one or more sensors configured to detect at least one of a cardio-vibrational signal, a pulmonary-vibrational signal, and a pulse oxygen level of the patient.

27. The ambulatory medical device of claim 16, wherein the secondary ECG monitoring circuitry comprises one of a three ECG lead telemetry device, a six ECG lead telemetry device, and a twelve ECG lead telemetry device.

28. The ambulatory medical device of claim 16, further comprising at least two therapy electrodes configured to be placed proximate to the patient's skin and further configured to deliver at least one therapeutic shock to the patient.

29. A signal processing system, comprising:
at least one physiological sensor configured to be placed proximate to a patient's skin and detect at least one raw physiological signal of the patient; and
a physiological signal processing node device comprising
physiological signal pre-processing circuitry operably connected to the at least one physiological sensor and configured to
receive the at least one raw physiological signal via the at least one physiological sensor; and
process the at least one raw physiological signal to produce a first physiological signal and a second physiological signal that is substantially the same as the first physiological signal;
first physiological signal conditioning circuitry configured to condition the first physiological signal and provide the conditioned first physiological signal to a primary patient monitoring device;
second physiological signal conditioning circuitry configured to be electrically isolated from the first physiological signal conditioning circuitry and configured to condition the second physiological signal; and
telemetry circuitry electrically coupled to the second physiological signal conditioning circuitry, the telemetry circuitry comprising a telemetry input configured to receive the conditioned second physiological signal;
telemetry simulation circuitry configured to simulate one or more physiological conditions of the patient based on the conditioned second physiological signal; and
a plurality of telemetry output connectors configured to provide one or more output telemetry signals based on the simulated one or more physiological signal conditions of the patient to a secondary physiological signal processing system.

30. The signal processing system of claim 29, wherein the telemetry simulation circuitry comprises one or more relays to disconnect the telemetry circuitry from the plurality of telemetry output connectors in response to at least one input from the primary patient monitoring device.

31. The signal processing system of claim 29, wherein the second physiological signal conditioning circuitry is further configured to filter out one or more electrical signals applied to the patient by the primary patient monitoring device.

32. The signal processing system of claim 29, wherein the telemetry circuitry is configured to receive at least one input from the primary patient monitoring device.

33. The signal processing system of claim 32, wherein the telemetry simulation circuitry is further configured to simulate the one or more physiological conditions of the patient based on the conditioned second physiological signal and the at least one input from the primary patient monitoring system.

34. The signal processing system of claim 33, further comprising a plurality of electrocardiogram (ECG) sensing electrodes configured to be placed proximate to a patient's skin and detect at least one raw ECG signal lead of the patient, and wherein the telemetry simulation circuitry is further configured to simulate one or more ECG signal conditions of the patient, and wherein the telemetry output connectors are further configured to provide the one or more output telemetry signals based on the simulated one or more ECG signal conditions of the patient.

* * * * *